United States Patent
Kawai et al.

(10) Patent No.: US 8,828,905 B2
(45) Date of Patent: Sep. 9, 2014

(54) POROUS BASE MATRIX HAVING FORMYL GROUP, ADSORBENT USING THE POROUS BASE MATRIX, METHOD FOR PRODUCTION OF THE POROUS BASE MATRIX, AND METHOD FOR PRODUCTION OF THE ADSORBENT

(75) Inventors: Yoshikazu Kawai, Settsu (JP); Naomi Kawahara, Settsu (JP)

(73) Assignee: Kaneka Corporation, Osaka (JP)

( * ) Notice: Subject to any disclaimer, the term of this patent is extended or adjusted under 35 U.S.C. 154(b) by 817 days.

(21) Appl. No.: 12/602,001

(22) PCT Filed: May 30, 2008

(86) PCT No.: PCT/JP2008/059986
§ 371 (c)(1),
(2), (4) Date: Nov. 25, 2009

(87) PCT Pub. No.: WO2008/146906
PCT Pub. Date: Dec. 4, 2008

(65) Prior Publication Data
US 2010/0184957 A1    Jul. 22, 2010

(30) Foreign Application Priority Data

May 30, 2007 (JP) ................................. 2007-143513
Jul. 19, 2007 (JP) ................................. 2007-188876
Jul. 19, 2007 (JP) ................................. 2007-188878

(51) Int. Cl.
| | | |
|---|---|---|
| B01J 20/26 | (2006.01) | |
| B01J 20/32 | (2006.01) | |
| B01D 15/00 | (2006.01) | |
| C07K 1/16 | (2006.01) | |
| B01J 20/289 | (2006.01) | |
| C07K 1/22 | (2006.01) | |

(52) U.S. Cl.
CPC ............... *C07K 1/16* (2013.01); *B01J 20/3219* (2013.01); *B01J 20/3274* (2013.01); *B01J 20/3212* (2013.01); *B01D 15/00* (2013.01); *B01J 20/289* (2013.01); *B01J 20/3242* (2013.01); *C07K 1/22* (2013.01)
USPC ..... 502/402; 530/387.1; 530/350; 536/123.1; 536/56

(58) Field of Classification Search
CPC . A61K 38/00; A61K 39/00; A61K 2039/505; C07K 14/47; C07K 2319/00; C07K 14/705; C07K 2317/24
USPC ........ 502/402; 536/123.1, 56; 530/387.1, 350
See application file for complete search history.

(56) References Cited

U.S. PATENT DOCUMENTS

| | | | |
|---|---|---|---|
| 4,882,226 | A | 11/1989 | Schutyser et al. |
| 5,151,350 | A | 9/1992 | Colbert et al. |
| 6,602,990 | B1 | 8/2003 | Berg |
| 2007/0243582 | A1 | 10/2007 | Kosugi et al. |

FOREIGN PATENT DOCUMENTS

| | | |
|---|---|---|
| JP | 62-155300 A | 7/1987 |
| JP | S62-153752 A | 7/1987 |
| JP | S63-90760 A | 4/1988 |
| JP | 1-217041 A | 8/1989 |
| JP | H5-18950 A | 1/1993 |
| JP | 6-98749 A | 4/1994 |
| JP | 6-281638 A | 10/1994 |
| JP | 2000-508361 A | 7/2000 |
| JP | 2006/004067 A1 | 1/2006 |

OTHER PUBLICATIONS

Greene et al., "Protective Group in Organic Synthesis", 2nd Edition, Index, pp. xi-xv.
Hermanson et al., "Immobilized Affinity Ligand Techniques", 1992, p. 72.
Hershko et al., "Removal of Pathogenic Autoantibodies by Immunoadsorption", Annals of the New York Academy of Science, vol. 1051, pp. 635-646, 2005.
Sanderson et al., "A Simple Method for Coupling Proteins to Insoluble Polysaccharides", Immunology, vol. 20, pp. 1061-1065, 1971.
Staudt et al., "Immunoadsorption in Dilated Cardiomyopathy: 6-Month Results from a Randomized Study", American Heart Journal, vol. 152, No. 4, 2006.
Steindl et al., "A Simple Method to Quantify Staphylococcal Protein A in the Presence of Human or Animal IgG in Various Samples", Journal of Immunological Methods, vol. 235, pp. 61-69, 2000.
Ken-ichi, Kasai, "Affinity Chromatography," Tokyo Kagaku Dojin (1991), 4 pages.

*Primary Examiner* — Colleen Dunn
*Assistant Examiner* — Haytham Soliman
(74) *Attorney, Agent, or Firm* — Birch, Stewart, Kolasch & Birch, LLP.

(57) ABSTRACT

The present invention relates to a porous base matrix having formyl group, which base matrix has a structure represented by the formula (2) as a spacer, which structure is obtained by cleaving a group represented by the formula (1):

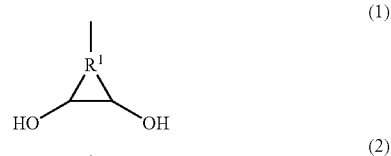

wherein, $R^1$ represents a group forming a five-membered ring or a six-membered ring with —CH(OH)—CH(OH)—; a method for producing the porous base matrix; and an adsorbent obtained by binding a ligand on the porous base matrix. By the present invention, a high-intensity base matrix for an adsorbent and an adsorbent are provided. The amount of a ligand leaked from the adsorbend is small.

11 Claims, No Drawings

POROUS BASE MATRIX HAVING FORMYL GROUP, ADSORBENT USING THE POROUS BASE MATRIX, METHOD FOR PRODUCTION OF THE POROUS BASE MATRIX, AND METHOD FOR PRODUCTION OF THE ADSORBENT

CROSS-REFERENCE TO RELATED APPLICATION

This application is the national phase of PCT/JP2008/059986 filed on May 30, 2008, which designated the United States.

TECHNICAL FIELD

The present invention relates to various adsorbent, especially to an adsorbent for treatment or medical use and an adsorbent for purifying an antibody drug.

BACKGROUND ART

Porous base matrix is used for a wide variety of adsorbents, for example, for adsorbents for chromatography or as affinity adsorbents. Of these, affinity adsorbents are able to efficiently purify a target substance or reduce the content of unwanted substances, and are therefore used as medical adsorbents or as adsorbents for purifying antibody drugs. In particular, attention has been focused on adsorbents obtained by immobilizing protein A as an affinity ligand on a porous base matrix as medical adsorbents for the treatment of rheumatism, hemophilia and dilated cardiomyopathy (for example, Non-patent Document 1, Non-patent Document 2).

Meanwhile, attention has been focused on adsorbents obtained by immobilizing protein A as an affinity ligand on a porous base matrix, i.e. adsorbents for purifying antibody drugs, as adsorbents able to specifically adsorb and release immunoglobulin (IgG). Methods for immobilizing a variety of affinity ligands such as protein A on a porous base matrix can be selected from among a variety of immobilization methods, such as cyanogen bromide method, trichlorotriazine method, epoxy method or tresyl chloride method, as indicated in Table 8.1 and FIG. 8.15 of Non-patent Document 3. Of these, it is preferable from an industrial perspective to use the reaction between a formyl group on a porous base matrix and an amino group on an affinity ligand so as to effect immobilization from the perspective of safety and for reasons such as the ease of the immobilization reaction and the fact that it is possible to use proteins or peptides produced by a relatively simple method.

A method in which a polysaccharide gel having vicinal hydroxy groups is oxidized through periodate oxidation so as to generate formyl groups on the sugar chain can be used as a method for introducing formyl groups into a porous base matrix (for example, refer to Non-patent Document 4). The porous base matrix is hereinafter abbreviated to a "sugar chain cleavage-type" porous base matrix. An adsorbent obtained via the method has the advantage of having little ligand leakage. In addition, it is possible to use a method that introduces formyl group via a variety of spacers obtained by, for example, a method that uses glutaraldehyde, such as that disclosed in FIG. 8.15 of Non-patent Document 3, or a method in which periodate is made to act on glyceryl group obtained through the ring opening of epoxy group, such as that disclosed in FIG. 8.15 of Non-patent Document 3 or FIG. 2.13 of Non-patent Document 5. The porous base matrix is hereinafter abbreviated to a "spacer-type" porous base matrix. The adsorbent using the spacer-type porous base matrix having formyl group tends to have relatively high adsorption of the target substance.

In addition, usage in direct hemoperfusion (DHP) methods is anticipated in the field of medical adsorbents for treatment, and it is hoped that base matrix and adsorbents that use base matrix has sufficient strength to withstand use in DHP. Meanwhile, the market for antibody drugs has expanded greatly in recent years; and as a result, upscaling and increased linear speed of antibody drug purification are being actively carried out. With the upscaling and increased linear speed of purification, a need has arisen for the strength of adsorbents, that is, porous base matrix, used in the purification to increase in some cases. If porous base matrix having low strength is used on a large scale and at high linear speeds, compaction of the porous base matrix can occur, which can lead to problems such as liquids being unable to flow. In the past, silica gel-based porous base matrix such as that disclosed in Patent Document 1, agarose-based crosslinked porous base matrix such as that disclosed in Patent Document 2 and cellulose-based porous base matrix such as that disclosed in Patent Document 3 have been known as porous base matrix having high strength.

Patent Document 1: JP6-281638A
Patent Document 2: JP2000-508361T
Patent Document 3: JP1-217041A
Non-patent Document 1: Annals of the New York Academy of Sciences, 2005, vol. 1051, p. 635-646
Non-patent Document 2: American Heart Journal, vol. 152, number 4, 2006
Non-patent Document 3: Affinity Chromatography, written by KASAI Kenichi et al., published by Tokyo Kagaku Dozin Co., Ltd., 1991
Non-patent Document 4: Immunology, 20, 1061, 1971
Non-patent Document 5: Immobilized Affinity Ligand Techniques, Greg T. Hermanson et al., 1992

DISCLOSURE OF THE INVENTION

Problems to be Solved by the Invention

In the mentioned above sugar chain cleavage-type porous base matrix having formyl group, the sugar chain is generally cleaved by a strong oxidation reaction, and there are cases where the strength of the porous base matrix is poor and use at high linear speeds is difficult. Moreover, the adsorbed quantity of antibody, which is the target substance, tends to be relatively small, and it is not easy to purify the antibody at high speed. Meanwhile, the spacer-type porous base matrix having formyl group is not desirable from the perspectives of safety and purity, since the affinity ligand may leak out during treatment or during purification of the target substance and contaminate either the patient's blood or the purified product if the introduced quantity of formyl groups is small.

In addition, silica gel-based porous base matrix, which is said to be high-strength porous base matrix, tends to adsorb a small quantity of the target substance and is often difficult to be used in alkaline conditions. Agarose-based crosslinked porous base matrix often involves complex crosslinking methods and is often expensive. Cellulose-based porous base matrix and cellulose-based crosslinked porous base matrix have few of the drawbacks such as those of glass-based porous base matrix and agarose-based crosslinked porous base matrix, but can suffer from compaction if used at the scales and linear speeds that have recently become the norm in antibody drug purification.

The present invention addresses the above-mentioned problems of the prior art, and aims to provide, at low cost, a formyl group-containing porous base matrix having high strength which increases safety during treatment and purification, achieves an increase in speed and further increases the purity of a purified product; an adsorbent that uses the porous base matrix; methods for producing the porous base matrix and adsorbent; and a purification method using the porous base matrix and adsorbent.

Means for Solving the Problems

The inventors of the present invention intensively studied for solving the above problem to complete the present invention.

The present invention relates to a porous base matrix having a formyl group, characterized in comprising a part represented by the general formula (2) in a spacer:

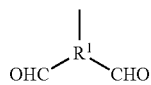

(2)

wherein, the definition of $R^1$ is the same as below,
wherein the part is induced from a group represented by the general formula (1):

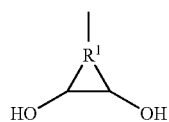

(1)

wherein, $R^1$ represents a group forming a five-membered ring or a six-membered ring with —CH(OH)—CH(OH)—.

The present invention also relates to a method for producing the above porous base matrix having the formyl group, characterized in comprising steps of obtaining a porous base matrix precursor introduced with a spacer having a part represented by the general formula (1), and cleaving the five-membered ring or six-membered ring to derive a group represented by the general formula (1).

The present invention also relates to a porous base matrix having a formyl group, characterized in comprising a group represented by the general formula (5):

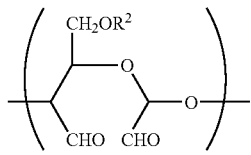

(5)

wherein, $R^2$ represents a hydrogen atom or a protective group for hydroxy group,
wherein the leak amount of a ligand from an adsorbent is 100 ppm or less when the ligand is immobilized on the porous base matrix to be the adsorbent.

The present invention also relates to a method for producing the above porous base matrix having the formyl group, characterized in comprising a step of reacting a periodate with a cellulose base matrix to oxidatively cleave the pyranose ring to introduce the formyl group.

The present invention also relates to an adsorbent, wherein an affinity ligand is bound on the porous base matrix having the formyl group.

The present invention also relates to a purification method wherein the adsorbent is used, and preferably relates to a method for purifying an immunoglobulin wherein the adsorbent having protein A as an affinity ligand is used.

Effect of the Invention

According to the present invention, a formyl group-containing porous base matrix having high strength is provided. The formyl group-containing porous base matrix of the present invention can be preferably used in an adsorbent, and an adsorbent that adsorbs a large quantity of a target substance and hardly suffers from ligand leakage can be obtained with the porous base matrix. In addition, according to the adsorbent of the present invention, it is also possible to increase safety during treatment and purification and to increase the speed and purity of treatment and purification.

Mode for Carrying Out the Invention

The inventors of the present invention found that it is possible to obtain an adsorbent having little ligand leakage and high adsorption of a target substance by using a formyl group-containing porous base matrix into which a spacer having a moiety represented by general formula (2) mentioned below, which is derived from the group represented by general formula (1) mentioned below, is introduced when an adsorbent having an affinity ligand is prepared.

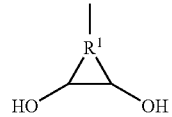

(1)

In the formula, $R^1$ represents a group that forms a 5- or 6-membered ring together with a —CH(OH)—CH(OH)—.

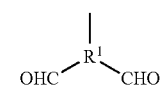

(2)

$R^1$ corresponds to $R^1$ in formula (1) mentioned above.

It is preferable from the perspective of decreased ligand leakage that the aforementioned formyl group and the amino group on the ligand can form a structure represented by general formula (3) or general formula (4) in cases where the formyl group-containing porous base matrix of the present invention immobilizes an amino group-containing ligand.

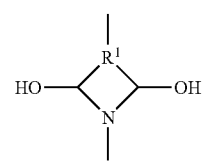

(3)

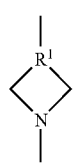

(4)

In the aforementioned formula (3) and formula (4), $R^1$ forms a 6- or 7-membered ring structure with the nitrogen atom, and corresponds to $R^1$ in the aforementioned formula (1).

$R^1$ is not particularly limited in any of the general formulae; and the type of atoms and number of atoms contained in $R^1$ and the length, number of branches and the like in $R^1$ are not limited; and a cyclic moiety or a double bond and/or a triple bond may be present. In addition, with regard to the parts not having atomic symbols displayed, the type of atom, the presence or absence of substituent group, the number of bonds, and the presence or absence of double and/or triple bonds are not limited, and two or more types of atom may be contained. In addition, any of the sites in the general formulae may be bonded to the porous base matrix or bonded to the porous base matrix via another compound.

The formyl group-containing porous base matrix of the present invention can be obtained by using, as a precursor, a porous base matrix into which a spacer having the structure represented by general formula (1) is introduced, and then treating the precursor base matrix with a periodate oxidation method and the like so as to convert the structure of the spacer to the structure represented by general formula (2).

The compound introduced as the spacer when the precursor is prepared can be used without any particular limitations insofar as the compound has a 5- or 6-membered ring structure represented by the aforementioned general formula (1). The type of ring structure can be a 5- or 6-membered ring of carbon only, such as cyclopentane or cyclohexane, or a sugar or sugar analogue such as furanose or pyranose, and sugars and sugar analogues are preferred for reasons such as ease of procurement. Furthermore, reducing sugar is particularly preferred from the perspective of easily obtaining the structure of general formula (3) or general formula (4).

In a case where a periodate oxidation method or the like is used as a method for introducing a formyl group, it is preferable that the compound having the ring structure represented by the aforementioned general formula (1) has a moiety in which successive carbon atoms are each bonded to a hydroxy group and the number of the successive carbon atoms is two at a maximum. This is because the content ratio of the structure represented by the aforementioned general formula (2) can readily increase and it is easy to form the structure represented by general formula (3) or general formula (4) when an amino group-containing ligand is immobilized.

Even in the case of a sugar or sugar analogue in which three or more successive carbon atoms are each bonded to a hydroxy group, if the sugar or sugar analogue has another moiety in which the number of such successive carbon atoms is two, such a sugar or sugar analogue is preferred since it is easy for the content ratio of the structure represented by the aforementioned general formula (2) to increase and it is easy to form the structure represented by general formula (3) or general formula (4) when an amino group-containing ligand is immobilized.

Moreover, in a case where glucose is used as a compound having the ring structure represented by the aforementioned general formula (1) and a formyl group is introduced using a periodate oxidation method, a linear spacer is obtained in theory and it is thought that there is a high probability that the spacer has a structure that is different from that of general formula (2), since glucose has a moiety in which three or more successive carbon atoms are each bonded to a hydroxy group and does not have another moiety in which two successive carbon atoms are each bonded to a hydroxy group. However, the use of glucose is not ruled out, since there can be cases in which the spacer has the structure of general formula (2) depending on the conditions under which introduction into the porous base matrix is carried out or the conditions under which the formyl group is introduced.

It is preferable to utilize a reaction between a functional group on a porous base matrix and a functional group on a sugar or sugar analogue as a method for introducing the sugar or sugar analogue into the porous base matrix. The functional group on the porous base matrix and the functional group on the sugar or sugar analogue are not particularly limited, and using a combination of functional groups that react with each other is preferred, and interposing another compound therebetween is also preferred.

When a porous base matrix into which an epoxy group and/or a formyl group is introduced is used as an intermediate, it is preferable that the sugar or sugar analogue has a functional group that can react with the epoxy group and/or formyl group.

The functional group that reacts with the epoxy group is not particularly limited insofar as being able to react with the epoxy group; and a hydroxy group, a thiol group and an amino group are generally can be exemplified. In a case where a porous base matrix into which an epoxy group is introduced is used as an intermediate, it is preferable that the sugar or sugar analogue contains at least one of the functional groups. A thiol group and an amino group are more preferred due to having little effect on the formylation of the spacer, which is a subsequent step; and an amino group is particularly preferred from the perspective of ease of procurement.

The functional group that reacts with the formyl group is not particularly limited insofar as being able to react with the formyl group; and an amino group is can be generally exemplified, and it is preferable that the sugar or sugar analogue contains an amino group when a porous base matrix into which a formyl group is introduced is used as an intermediate.

Specifically, it is more preferable that a sugar or sugar analogue introduced into a porous base matrix contains at least a thiol group and/or an amino group.

Amino group-containing sugars, i.e. amino sugars, are not particularly limited. One or more selected from glucosamine, galactosamine, annosamine, lactosamine, fucosamine, mannosamine, meglumine, allosamine, altrosamine, ribosamine, arabinosamine, gulosamine, idosamine, talosamine, xylosamine, lyxosamine, sorbosamine, tagatosamine, psicosamine, fructosamine, iminocyclitol, mucopolysaccharides, glycoproteins, hyaluronic acid, heparin, chondroitin, chondroitin 4-sulfate, dermatan sulfate; D-isomers, L-isomers and racemates thereof; polysaccharide, polymer, glycolipid and the like which contain these as a constituent component; or salts such as hydrochlorides thereof can be exemplified.

Of these, glucosamine and derivatives thereof are more preferred. This is because the structure represented by the above-mentioned general formula (2) can be obtained relatively efficiently, and it is easy to form a structure represented by general formula (3) or general formula (4) when an amino group-containing ligand is immobilized, and also because glucosamine and derivatives thereof can be easily procured. Either the D-isomer or L-isomer of glucosamine can be used, and the D-isomer is more preferred.

The method for producing the glucosamine able to be used in the present invention is not particularly limited, and it is preferable to obtain the glucosamine by chemically modifying glucose and the like; and glucosamine derived from shells of crustaceans and the like, chitin, chitosan and the like is more preferred; and glucosamine able to be obtained from plant-based compounds and the like, such as the so-called fermented glucosamine manufactured by Kyowa Hakko Kogyo Co., Ltd., are particularly preferred. In addition, the glucosamine able to be used in the present invention is preferably in the form of a salt such as a hydrochloride for reasons of solubility.

The quantity of the sugar or sugar analogue introduced into the porous base matrix is preferably not less than 1 μmol and not more than 500 μmol relative to 1 mL of the porous base matrix. It is preferable that the introduced quantity of sugar or sugar analogue is 1 μmol or more relative to 1 mL of the porous base matrix from the perspective of increasing the adsorbed quantity of target substance when the porous base matrix is used as an adsorbent, and it is preferable that the introduced quantity of sugar or sugar analogue is 500 μmol or less in order to reduce the manufacturing costs of the porous base matrix of the present invention.

The introduced quantity of sugar or sugar analogue is more preferably not less than 3 μmol and not more than 250 μmol, further preferably not less than 6 μmol and not more than 125 μmol, particularly preferably not less than 10 μmol and not more than 70 μmol, and most preferably not less than 10 μmol and not more than 30 μmol, relative to 1 mL of the porous base matrix. The introduced quantity of sugar or sugar analogue can be determined by measuring the reduction in quantity of the sugar or sugar analogue in the reaction solution after the introduction reaction is completed, by titration such as non-aqueous titration onto the porous base matrix after the reaction, or by elemental analysis.

When a sugar or sugar analogue is introduced into the porous base matrix, the quantity of the sugar or sugar analogue to be used is not particularly limited; but the quantity is preferably 0.01 mol or higher relative to the functional group in the porous base matrix in order to obtain a more appropriate introduction quantity, and is preferably 100 mol or lower from the perspectives of waste fluid disposal and efficiency. The quantity is more preferably not less than 0.1 mol and not more than 10 mol, further preferably not less than 0.5 mol and not more than 5 mol, and particularly preferably not less than 1 mol and not more than 2.5 mol.

The solvent used when sugar or sugar analogue is introduced into the porous base matrix is not particularly limited; and water, commonly used organic solvents such as heptane, dimethyl sulfoxide, dimethyl formamide and dioxolane, alcohols such as ethanol, methanol and propanol, or a mixed solvent of two or more thereof can be used.

The pH during the introduction reaction is not particularly limited; but it is preferable to carry out the reaction at pH of 3 or higher from the perspective of reaction efficiency, and the pH is preferably 13 or lower for reasons such as loss of activity of the functional group and damage to the porous base matrix. The pH is more preferably not lower than 4 and not higher than 12, further preferably not lower than 6 and not higher than 11, particularly preferably not lower than 7 and not higher than 10, and most preferably not lower than 8 and not higher than 10.

The temperature when sugar or sugar analogue is introduced into the porous base matrix is not particularly limited; but the temperature is preferably 0° C. or higher due to being advantageous in terms of the reaction rate, preferably 100° C. or lower from the perspectives of safety and damage to the base matrix, and more preferably 70° C. or lower from the perspective of the functional groups not losing activity. The temperature is more preferably not lower than 4° C. and not higher than 60° C., further preferably not lower than 10° C. and not higher than 50° C., particularly preferably not lower than 15° C. and not higher than 40° C., and most preferably not lower than 25° C. and not higher than 40° C.

It is preferable that the introduction reaction is carried out under stirring or shaking, and the number of revolution or vibration per minute is not particularly limited, but the number is preferably not less than 1 rpm and not more than 1000 rpm, more preferably not less than 10 rpm and not more than 500 rpm, further preferably 30 rpm and not more than 300 rpm, particularly preferably not less than 50 rpm and not more than 200 rpm, most preferably not less than 75 rpm and not more than 150 rpm, since uniform stirring is possible and for reasons such as not causing physical damage to the base matrix. It is particularly preferred to adjust the stirring rate according to differences in the specific gravities of the raw materials and the strength of the base matrix.

The reaction time when sugar or sugar analogue is introduced into the porous base matrix is not particularly limited, but the time is preferably not less than 0.2 hours and not more than 100 hours, more preferably not less than 0.5 hours and not more than 50 hours, further preferably not less than 1 hour and not more than 24 hours, particularly preferably not less than 2 hours and not more than 20 hours, and most preferably not less than 3 hours and not more than 12 hours, from the perspectives of loss of activity of the functional groups and damage to the base matrix. It is particularly preferred that the reaction time is adjusted according to the reactivity, pH and reaction temperature.

The method for introducing sugar or sugar analogue into the porous base matrix is not particularly limited; but it is preferable to use the porous base matrix into which an epoxy group is introduced, as an intermediate. It is thought that a method in which the epoxy group on the porous base matrix of the intermediate reacts with the sugar or sugar analogue is preferred due to being simple and achieving a good reaction efficiency.

The method for introducing epoxy group into the porous base matrix is not particularly limited, but can be carried out using publicly known techniques.

For example, it is possible to introduce epoxy group by allowing at least one halohydrin, such as epichlorohydrin, epibromohydrin or dichlorohydrin, or bifunctional or higher epoxy compound, such as resorcinol diglycidyl ether, neopentylglycol diglycidyl ether, 1,6-hexanediol diglycidyl ether, hydrogenated bisphenol A diglycidyl ether, glycerol diglycidyl ether, trimethylolpropane diglycidyl ether, diglycidyl terephthalate, diglycidyl ortho-phthalate, ethylene glycol diglycidyl ether, diethylene glycol diglycidyl ether or propylene glycol diglycidyl ether, to act on the porous base matrix. It is preferable to allow the bifunctional or higher epoxy compound to act on the porous base matrix, since the porous base matrix is crosslinked and becomes stronger.

Of these, it is preferable to use epichlorohydrin from the perspectives of cost and safety, and to use a glycidyl ether compound such as glycerol polyglycidyl ether or diglycerol polyglycidyl ether from the perspectives of strength and solubility.

The use quantity of the epoxidizing agent is not particularly limited; but the quantity is preferably 0.01 times or more relative to the volume of the base matrix in order to achieve a more appropriate epoxy group introduction quantity, and/or is preferably 10 times or less relative to the volume of the base matrix from the perspectives of waste fluid disposal and efficiency. The quantity is more preferably not less than 0.05 times and not more than 5 times, further preferably not less than 0.1 times and not more than 3 times, particularly preferably not less than 0.1 times and not more than 1 times, and most preferably not less than 0.1 times and not more than 0.5 times.

The solvent to be used when the epoxidation reaction is carried out is not particularly limited; but water, commonly used organic solvents such as heptane, dimethyl sulfoxide, dimethyl formamide and dioxolane, alcohols such as ethanol, methanol and propanol, or a mixed solvent of two or more thereof can be used.

It is preferable to carry out the reaction under alkaline conditions from the perspective of reaction efficiency. In addition, carrying out the reaction in the presence of a reducing agent such as sodium borohydride is more preferred in order to shorten the reaction time.

The temperature when the epoxidation reaction is carried out is not a particular problem; but the temperature is preferably 0° C. or higher due to being advantageous in terms of the reaction rate, and/or preferably 100° C. or lower from the perspectives of safety and damage to the base matrix, more preferably 70° C. or lower from the perspective of the functional groups not losing activity, further preferably not lower than 4° C. and not higher than 60° C., particularly preferably not lower than 25° C. and not higher than 50° C., and most preferably not lower than 25° C. and not higher than 40° C.

It is preferable that the epoxy group introduction reaction is carried out under stirring or shaking; and the number of revolution or vibration per minute is not particularly limited, but the number is preferably not less than 10 rpm and not more than 1000 rpm, more preferably not less than 30 rpm and not more than 500 rpm, particularly preferably not less than 50 rpm and not more than 300 rpm, and most preferably not less than 75 rpm and not more than 150 rpm, since uniform stirring is possible and for reasons such as not causing physical damage to the base matrix. It is particularly preferable that the number is adjusted according to the differences in the specific gravities of the raw materials and the strength of the base matrix.

The epoxidation reaction time is not particularly limited; but the time is preferably not less than 1 hour and not more than 8 hours when a halohydrin is used, and preferably not less than 2 hours but less than 15 hours when a bifunctional or higher epoxy compound such as a bis-epoxide (bis-oxirane) or a polyepoxide (polyoxirane) is used, from the perspectives of loss of activity of the epoxy groups and damage to the base matrix. The reaction time is more preferably adjusted according to the reactivity of the epoxidizing agent, the pH or the reaction temperature.

The epoxy content of the intermediate of the porous base matrix of the present invention is preferably not less than 2 µmol and not more than 150 µmol relative to 1 mL of the porous base matrix. Introducing 2 µmol or more of epoxy group is preferable due to ease of introduction of sugar or sugar analogue, and introducing 150 µmol or less is preferable in order to inhibit multi-point binding between the sugar or sugar analogue and the porous base matrix and non-specific adsorption during antibody purification. In addition, the reason is not clear, but introducing not more than 150 µmol of epoxy group is preferable due to the degree of adsorption increasing when the porous base matrix is used as an adsorbent. In addition, the epoxy content of the intermediate of the porous base matrix of the present invention is more preferably not less than 5 µmol and not more than 100 µmol, particularly preferably not less than 7.5 µmol and not more than 50 µmol, and most preferably not less than 15 µmol and not more than 35 µmol, relative to 1 mL of the porous base matrix.

In the present invention, the sugar or sugar analogue which has the structure represented by the above-mentioned general formula (1) and is introduced into the porous base matrix is converted into the formyl group represented by the above-mentioned general formula (2). Periodate oxidation can be used as the type of such a method. It is preferable to introduce formyl group by using a periodate such as sodium periodate or potassium periodate. The method is preferably used, since it is easy to obtain formyl group that can form a structure represented by general formula (3) or general formula (4) when an amino group-containing ligand is immobilized.

There is a tendency for glyceryl group, that is, vicinal hydroxy group, to be generated, when the porous base matrix into which the aforementioned epoxy group is introduced is used as an intermediate or when the porous base matrix is crosslinked by using a crosslinking agent that has the below-mentioned epoxy group as a functional group. Therefore, formyl group that do not easily form the structure represented by general formula (3) or general formula (4) can be generated, when periodate oxidation is used and an amino group-containing ligand is subsequently immobilized. From the perspective, it is preferable to block the glyceryl group or subject the glyceryl group to treatment such as degradation before sugar or sugar analogue is introduced into the porous base matrix.

The method for treating glyceryl group is not particularly limited; and a method that uses the requisite minimum quantity of an epihalohydrin, bifunctional or higher epoxy compound, crosslinking agent and the like or a method that achieves etherification or esterification by using a halogenated compound such as methyl iodide, ethyl iodide, another alkyl iodide, dibromopropane or another dibromoalkane can be exemplified.

It is also preferable to use a method in which glyceryl group is converted into a formyl group (that is, a monoformyl group) in advance with the use of a periodate salt and the like before sugar or sugar analogue is introduced into the porous base matrix. It is preferable that a glyceryl group is converted into a monoformyl group with the action of a periodate salt, since it is possible to directly introduce the sugar or sugar analogue into the monoformyl group.

It is preferable to allow monoethanolamine or a compound having an amino group, such as glycine, to act on a portion in which the monoformyl group is present in excess so as to effect blocking. In addition, a method in which a monoformyl group is converted into a hydroxy group by, for example, allowing a reducing agent such as sodium borohydride to act on the monoformyl group is also preferred. When a monoformyl group is converted into a hydroxy group, it is preferable to use a method in which the requisite minimum quantity of an epihalohydrin or bifunctional or higher epoxy compound is allowed to act on the hydroxy group so as to produce an intermediate into which an epoxy group is introduced and a sugar or sugar analogue is then introduced.

It is also preferable to combine and/or repeat the methods described above. Specifically, it is preferable to use the porous base matrix into which formyl group obtained by treating glyceryl group in advance with periodate salt is introduced as an intermediate.

Of these, it is particularly preferable as the method for treating glyceryl group that a halogenated alcohol or a monofunctional epoxy compound is allowed to act on the glyceryl group. When the method is used, active sites at which sugar or sugar analogue can be introduced may not lost since the hydrophilicity of the porous base matrix is hardly reduced and hydroxy groups remain even after the glyceryl group is treated, and the strength of the porous base matrix is not reduced even if vicinal hydroxy group is present in the substrate of the porous base matrix. The method is therefore preferred.

Specifically, it is preferable to use the porous base matrix on which halogenated alcohol and/or monofunctional epoxy compound is allowed to act, as an intermediate. The halogenated alcohol to act on glyceryl group is not particularly limited; but can be, for example, chloromethanol, bromomethanol, iodomethanol, 2-iodoethanol, 2-chloroethanol, 2-bromoethanol, 2-chloro-1-propanol, 3-chloro-1-propanol, 3-bromo-1-propanol, 1,3-dichloro-2-propanol, 1-chloro-2-methyl-2-propanol, 2-chloroethanol, 3-chloropropanol, 4-chlorobutanol, 5-chloropentanol, 6-chlorohexanol, 9-chlorononanol, trifluoroethanol, trichloroethanol, 2,2-dichloroethanol, 1-chloro-2-propanol, 2,2-dibromoethanol, 2,2,2-tribromoethanol, 2-fluoroethanol, 2-chlorocyclohexanol, 2-chlorocyclopentanol, ortho-, meta- or para-chlorophenol, pentafluoropropanol, tetrafluoropropanol, hexafluoroisopropanol, heptafluorobutanol, nonafluoro-t-butanol, octafluoropentanol, 6-chloro-1-hexanol, 6-bromo-1-hexanol, 4-chloro-1-butanol, 3-chloro-2,2-dimethyl-1-propanol, tetrafluoropropanol, tetrafluorobutanol, tetrafluoropentanol, tetrafluoroheptanol, tetrafluorooctanol, pentafluoropropanol, pentafluorobutanol, pentafluoropentanol, pentafluoroheptanol, pentafluorooctanol, hexafluoropropanol, hexafluorobutanol, hexafluoropentanol, hexafluoroheptanol, hexafluorooctanol, heptafluoropropanol, heptafluorobutanol, heptafluoropentanol, heptafluoroheptanol, heptafluorooctanol, tetrachloroethanol, chloroheptanol, 2,2,2-trichloroethanol, tribromoethanol, 1,3-dichloro-2-propanol, 1,1,1-trichloro-2-propanol, di(iodohexamethylene)aminoisopropanol, tribromo-t-butyl alcohol alkylene oxide, or a combination of two or more thereof.

Iodinated alcohols are more preferred as halogenated alcohols; and of these, iodomethanol and 2-iodoethanol are particularly preferred due to preventing the porous base matrix from becoming hydrophobic.

The monofunctional epoxy compound that acts on glyceryl group is not particularly limited; but can be, for example, ethylene oxide, propylene oxide, butylene oxide, amylene oxide, hexylene oxide, tetrahydrofuran, 4-vinylcyclohexene monoepoxide, norbornene monoepoxide, limonene monoepoxide, phenyl glycidyl ether, monoepoxidated 4-vinylcyclohexene, methyl glycidyl ether, ethyl glycidyl ether, butyl glycidyl ether, 2-ethylhexyl glycidyl ether, cyclohexyl glycidyl ether, methoxyethyl glycidyl ether, p-tert-butyl glycidyl ether, butyl glycidyl ether, 2-ethylhexyl glycidyl ether, an aryl glycidyl ether, 1,2-butylene oxide, 1,3-butadiene monooxide, 1,2-dodecylene oxide, 1,2-epoxydecane, styrene oxide, cyclohexene oxide, 3-methacryloyloxymethyl cyclohexene oxide, 3-vinylcyclohexene oxide, 4-vinylcyclohexene oxide, p-tert-butylphenyl glycidyl ether, dibromophenyl glycidyl ether or a combination of two or more thereof.

Alkylene oxides are more preferred as monofunctional epoxy compound; and of these, ethylene oxide, propylene oxide and butylene oxide are particularly preferred due to preventing the porous base matrix from becoming hydrophobic; and butylene oxide is most preferred from the perspective of safety. The conditions and detailed production method for the reaction in which the halogenated alcohol or monofunctional epoxy compound is allowed to act on glycidyl group are not particularly limited; but the reaction can be carried out in the same way as the aforementioned epoxy group introduction reaction. Furthermore, it is preferable to use an onium salt such as KI, Bu$_4$NI and the like as a catalyst from the perspective of improving reactivity.

Porous base matrix is widely used as adsorbents for a variety of chromatographic methods and affinity adsorbents, including medical adsorbents for treatment; and upscaling and increased linear speed of antibody drug purification is being actively carried out as a result of a significant increase in the antibody drug market in the field of antibody drug purification in particular. With the upscaling and increased linear speed of purification, a need has arisen for the strength of adsorbents, that is, porous base matrix, used in the purification to increase in some cases. Method for increasing the strength of porous base matrix is not particularly limited, and methods such as increasing the matrix content (for example, the resin content) of the porous base matrix are preferred, but increasing the strength of the porous base matrix by using a crosslinking agent is more preferred due to the advantage of being difficult for the diameter of the pores in the porous base matrix to become smaller. In other words, it is preferable for the porous base matrix of the present invention to be crosslinked.

The crosslinking agent and crosslinking conditions are not particularly limited, and publicly known techniques can be used. For example, it is possible to carry out the crosslinking by using at least one halohydrin, such as epichlorohydrin, epibromohydrin or dichlorohydrin, or bifunctional or higher epoxy compound, such as resorcinol diglycidyl ether, neopentylglycol diglycidyl ether, 1,6-hexanediol diglycidyl ether, hydrogenated bisphenol A diglycidyl ether, glycerol diglycidyl ether, trimethylolpropane diglycidyl ether, diglycidyl terephthalate, diglycidyl ortho-phthalate, ethylene glycol diglycidyl ether, diethylene glycol diglycidyl ether or propylene glycol diglycidyl ether.

The method for increasing the strength of the porous base matrix by using the crosslinking agent is not particularly limited, but it is preferable that the crosslinking agent is allowed to act on the base matrix under alkaline condition from the perspective of reaction efficiency. The method for charging the crosslinking agent is not particularly limited, and the entire usage quantity thereof may be added at the start of the reaction, the divided quantities may be charged into multiple times and the reactions are repeated, the crosslinking agent may be charged in small portions using an addition funnel and the like, or the porous base matrix may be charged in a reaction vessel in which the crosslinking agent is charged.

The solvent to be used when the crosslinking reaction is carried out is not particularly limited; and water, commonly used organic solvents such as heptane, dimethyl sulfoxide, dimethyl formamide and dioxolane, alcohols such as ethanol, methanol and propanol, or a mixed solvent of two or more thereof can be used. In addition, it is preferable to carry out the reaction in the presence of a reducing agent such as sodium borohydride in order to increase the reaction efficiency.

The temperature during the crosslinking reaction is not particularly limited; but the temperature is preferably 0° C. or higher due to being advantageous in terms of the reaction rate and/or is preferably 100° C. or lower from the perspectives of safety and damage to the porous base matrix, and more preferably 70° C. or lower from the perspective of the functional groups not losing activity.

It is preferable that the crosslinking reaction is carried out under stirring or shaking, and the number of revolution or vibration per minute is not particularly limited, but the number is preferably not less than 1 rpm and not more than 1000 rpm since uniform stirring is possible and for reasons such as not causing physical damage to the porous base matrix, more preferably not less than 10 rpm and not more than 500 rpm, further preferably not less than 30 rpm and not more than 300 rpm, particularly preferably not less than 50 rpm and not more than 200 rpm, most preferably not less than 75 rpm and not more than 150 rpm. It is preferable to adjust the stirring rate according to the differences in the specific gravities of the raw materials and the strength of the porous base matrix.

The crosslinking reaction time is not particularly limited, but the reaction time is preferably not less than 1 hour and not more than 8 hours when a halohydrin is used from the perspectives of loss of activity of the functional groups and damage to the base matrix, and preferably not less than 1 hour but less than 15 hours when a bifunctional or higher epoxy compound is used. It is more preferably to adjust the reaction time according to the reactivity of the crosslinking agent, the pH or the reaction temperature.

The material of the porous base matrix of the present invention is not particularly limited; but can be, for example, a polysaccharide, polystyrene, a styrene-divinylbenzene copolymer, polyacrylamide, poly(acrylic acid), poly(methacrylic acid), a poly(acrylic ester), a poly(methacrylic ester), poly(vinyl alcohol), derivatives thereof and the like. The materials may have a coating layer of, for example, a polymer material having a hydroxy group, such as hydroxyethyl methacrylate, or a graft copolymer obtained by copolymerizing a monomer having a poly(ethylene oxide) chain with another polymerizable monomer. Of these, polysaccharides, poly(vinyl alcohol) and the like can be preferably used due to allowing easy introduction of active groups into the base matrix surface.

Of these, it is more preferable that the porous base matrix of the present invention contains polysaccharide. Polysaccharides are preferred due to being easily industrially obtained and having high safety to organisms. Polysaccharides able to be used in the porous base matrix of the present invention are not particularly limited; but can be, for example, agarose, cellulose, dextrin, chitosan, chitin, derivatives thereof and the like.

It is more preferable that the porous base matrix of the present invention contains cellulose and/or cellulose derivative. The porous base matrix containing cellulose or a cellulose derivative is preferred due to having relatively high mechanical strength, hardly being damaged and becoming particulate due to toughness, and suffering from relatively little compaction even when flushed with a liquid at high speed in case of being charged in a column. In addition, cellulose is most preferred as the material for the porous base matrix of the present invention from the perspectives of strength and cost.

The present invention also relates to a porous base matrix having a formyl group, characterized in comprising a group represented by the general formula (5):

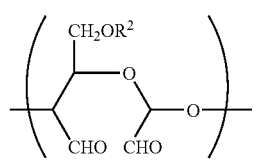

(5)

wherein, $R^2$ represents a hydrogen atom or a protective group for hydroxy group, wherein the leak amount of a ligand from an adsorbent is 100 ppm or less when the ligand is immobilized on the porous base matrix to be the adsorbent.

The protecting group for hydroxy group, i.e. $R^2$, in the present invention can be selected from among the groups disclosed in Protective Group in Organic Synthesis, second edition, published by John Wiley & Sons, Inc.

The protecting group for hydroxy group, i.e. $R^2$, can be an acyl group, an alkyl group, a carboxymethyl group, a carboxyethyl group, a cyanoethyl group, an aminoethyl group, a nitro group, a sulfo group, a phosphate group and the like. The acyl group includes saturated or unsaturated, straight chain or branched chain group having 1-10 carbon atoms, and is exemplified by an acetyl group. The alkyl group includes saturated or unsaturated, straight chain or branched chain group having 1-10 carbon atoms, and is exemplified by a methyl group or an ethyl group.

The inventors of the present invention found that it is possible to reduce the amount of ligand leakage and increase the purity of a purification target substance by using the formyl group-containing porous base matrix having a site represented by general formula (5) and characterized in that the amount of ligand leakage of an adsorbent obtained by immobilizing the ligand on the porous base matrix is not more than 100 ppm. Moreover, the amount of ligand leakage is defined as the ratio of ligand relative to purification target substance in the present invention.

The porous base matrix of the present invention more preferably contains cellulose and/or cellulose derivative. The porous base matrix containing cellulose or cellulose derivative is preferred due to having relatively high mechanical strength, hardly being damaged and becoming particulate due to toughness, and suffering from relatively little compaction even when flushed with a liquid at a high linear speed in case of being charged in a column. In addition, cellulose is most preferred as the material for the porous base matrix of the present invention from the perspectives of strength and cost.

The method for introducing the formyl group that forms the structure represented by general formula (5) into the porous base matrix is not particularly limited; but a method in which a periodate salt such as sodium periodate or potassium periodate is allowed to act on the porous base matrix is preferred. In addition, a method in which a periodate salt is allowed to act on a cellulose base matrix so as to achieve oxidative cleavage of a pyranose ring and thereby introduce formyl group is more preferred. The conditions for formylation using a periodate salt are the same as those used when the structure represented by the aforementioned general formula (1) is converted into the structure represented by general formula (2).

The formyl group content of the porous base matrix of the present invention is preferably not less than 1 μmol and not more than 200 μmol relative to 1 mL of the porous base matrix. When the formyl group content is not less than 1 μmol relative to 1 mL of the porous base matrix, it is possible to efficiently immobilize an affinity ligand, and to increase the adsorbed quantity of the purification target substance in case of using the porous base matrix as an adsorbent. In addition, the reason is unclear, but surprisingly, the formyl group content is preferably not more than 200 μmol relative to 1 mL of the porous base matrix from the perspective of increasing the adsorbed quantity of the purification target substance. In addition, in case of using a method in which formyl group is introduced through the action of a periodate salt, the strength of the porous base matrix is readily increased when the formyl group content is not more than 200 μmol relative to 1 mL of the porous base matrix.

The formyl group content is more preferably not less than 2 μmol and not more than 100 μmol, further preferably not less than 4 μmol and not more than 70 μmol, particularly preferably not less than 7 µmol and not more than 40 µmol, and most preferably not less than 10 µmol and not more than 25 µmol, relative to 1 mL of the porous base matrix.

The formyl group content can be adjusted according to, for example, the time and temperature of the formyl group introduction reaction and the concentration of the formylating agent such as a periodate salt. The formyl group content can be easily determined as the quantity of phenyl hydrazine adsorbed on the porous base matrix. Specifically, the formyl group content can be calculated by bringing 2 mL of the porous base matrix substituted with a 0.1M phosphate buffer at pH 8 into contact with 2 mL of a 0.1 M phosphate buffer solution at pH 8 in which phenyl hydrazine is dissolved, stirring at 40° C. for 1 hour, and then measuring the absorbance of the absorption maximum near 278 nm of the supernatant of the reaction liquid by UV detection. The quantity of phenyl hydrazine adsorbed on the porous base matrix is obtained from the absorbance, and the quantity is taken as the formyl group content of the porous base matrix. In such a case, the quantity of phenyl hydrazine to be charged is made to be twice the molar quantity of the expected formyl group content; and if the adsorbed quantity on the porous base matrix is not more than 25% or not less than 75% of the charged quantity of phenyl hydrazine, the charged quantity of phenyl hydrazine is revised and the measurement is repeated.

The resin content of the porous base matrix of the present invention is preferably not less than 3% and not more than 50%. When the resin content is not less than 3%, it is possible to obtain the porous base matrix that does not suffer from compaction even if used for purification on a large scale and at high linear speeds. When the resin content is not more than 50%, it is possible to ensure there are sufficient pores to allow the purification target substance to pass through. The resin content is more preferably not less than 5% and not more than 40%, further preferably not less than 6% and not more than 20%, and most preferably not less than 6% and not more than 15%. The resin content can be obtained as follows.

1) The porous base matrix is charged under settling until the volume thereof can be reduced no further, and the quantity thereof is adjusted so that the volume thereof is 1 mL.

2) Water is removed from the porous base matrix slurry until water is not bumped by heating, the slurry is then dried by heating at 105° C. for 15 hours, and the dry weight (g) of 1 mL of the porous base matrix is then measured.

3) The dry weight percentage, that is, the resin content, in 1 mL of the porous base matrix is then calculated. Resin content (%)=dry weight (g) of porous base matrix/volume (mL) of porous base matrix before drying×100.

The porous base matrix of the present invention preferably has a compressive stress of not less than 0.006 MPa and not more than 1 MPa when compressed by 5%, a compressive stress of not less than 0.015 MPa and not more than 3 MPa when compressed by 10%, and a compressive stress of not less than 0.03 MPa and not more than 5 MPa when compressed by 15%.

When the porous base matrix has a compressive stress of not less than 0.006 MPa when compressed by 5%, a compressive stress of not less than 0.015 MPa when compressed by 10% and a compressive stress of not less than 0.03 MPa when compressed by 15%, such a porous base matrix does not suffer from compaction even when a liquid is passed through at a high linear speed. In addition, in a case where the porous base matrix of the present invention preferably has a compressive stress of not more than 1 MPa when compressed by 5%, a compressive stress of not more than 3 MPa when compressed by 10% and a compressive stress of not more than 5 MPa when compressed by 15%, it is possible to reduce the brittleness of the porous base matrix and inhibit the generation of fine particles. The porous base matrix of the present invention more preferably has a compressive stress of not less than 0.008 MPa and not more than 1 MPa when compressed by 5%, a compressive stress of not less than 0.02 MPa and not more than 3 MPa when compressed by 10%, and a compressive stress of not less than 0.04 MPa and not more than 5 MPa when compressed by 15%.

In the preset invention, the compressive stress when compressed by 5% means the stress when the porous base matrix is compressed so that the volume thereof is reduced by 5% compared to the initial volume, the compressive stress when compressed by 10% means the stress when the porous base matrix is compressed so that the volume thereof is reduced by 10% compared to the initial volume, and the compressive stress when compressed by 15% means the stress when the porous base matrix is compressed so that the volume thereof is reduced by 15% compared to the initial volume. The initial volume means the volume of the porous base matrix charged under settling until the volume of the porous base matrix can be reduced no further by agitating a slurry that contains the porous base matrix. The compressive stress when compressed can be measured using the following method.

1) A slurry containing 50 vol % of the porous base matrix is placed in a glass measuring cylinder having an internal diameter of 15 mm.

2) The glass measuring cylinder is agitated so as to settle the porous base matrix until the volume thereof can be reduced no further, and the quantity of the porous base matrix is then adjusted so that the volume thereof is 4 mL. The volume at this point is used as the initial volume.

3) A metal piston which is processed so as not to generate friction on the inner wall of the measuring cylinder and not to allow the porous base matrix to leak out is attached to an autograph (EZ-TEST, manufactured by Shimadzu), on which a 20 N load cell is mounted.

4) The bottom surface of the piston is moved to a position corresponding to 120 vol % of the porous base matrix.

5) The piston is lowered at a test rate of 5 mm/min so as not to introduce bubbles, thereby compressing the porous base matrix and reducing the volume thereof.

6) The compressive stress is measured at an arbitrary point.

The volume average particle diameter of the porous base matrix of the present invention is preferably not less than 20 µm and not more than 300 µm. The volume average particle diameter of the porous base matrix is preferably not less than 20 µm from the perspective of preventing compaction, and is preferably not more than 300 µm from the perspective of increasing the adsorbed quantity of target substance when the porous base matrix is used as an adsorbent. The volume average particle diameter of the porous base matrix of the present invention is more preferably not less than 40 µm and not more than 200 µm, further preferably not less than 60 µm and not more than 150 µm, particularly preferably not less than 75 µm and not more than 100 µm, and most preferably not less than 80 µm and not more than 95 µm. The volume average particle diameter can be obtained by measuring the diameters of 100 particles of the porous base matrix selected at random. The diameters of the individual porous base matrix particles can be measured by taking microphotographs of the individual particles, storing the microphotographs as electronic data, and then using particle diameter measurement software (Image-Pro Plus, produced by Media Cybernetics).

The inventors of the present invention also provide an adsorbent that uses the above-mentioned porous base matrix of the present invention. The porous base matrix of the present invention can be used in an adsorbent. Adsorbents able to use the porous base matrix of the present invention are not particularly limited, and can be adsorbents for purifying antibodies, adsorbents for purifying antibody drugs, medical adsorbents for treatment, affinity adsorbents, and adsorbents for chromatography techniques such as affinity chromatography, ion exchange chromatography, hydrophobic interaction chromatography, gel filtration chromatography and hydroxyapatite chromatography. In order to use the porous base matrix of the present invention as an adsorbent, an affinity ligand is often immobilized on the porous base matrix. Affinity ligands able to be immobilized are not particularly limited, and it is possible to immobilize a desired affinity ligand and to use in a medical adsorbent for treatment or an adsorbent for purifying an antibody drug.

The quantity of affinity ligand introduced into the adsorbent of the present invention is preferably not less than 1 mg and not more than 1000 mg relative to 1 mL of the porous base matrix. The introduced quantity of affinity ligand is preferably not less than 1 mg relative to 1 mL of the porous base matrix from the perspective of increasing the adsorbed quantity of target substance, and is preferably not more than 1000 mg from the perspective of limiting production costs. The introduced quantity of affinity ligand is more preferably not less than 2 mg and not more than 120 mg, further preferably not less than 3 mg and not more than 60 mg, particularly preferably not less than 4 mg and not more than 30 mg, and most preferably not less than 5 mg and not more than 15 mg, relative to 1 mL of the porous base matrix. The introduced quantity of affinity ligand can be obtained by measuring the absorbance from the affinity ligand in the supernatant of the reaction liquid after the immobilization reaction. In addition, the introduced quantity of affinity ligand can be obtained by elemental analysis. For example, in the case of an amino group-containing affinity ligand, it is possible to measure the introduced quantity of affinity ligand by subjecting the adsorbent to nitrogen content analysis. In addition, it is possible to obtain the quantity of ligand by quantitatively determining the quantity of amino groups by titration.

The quantity of affinity ligand introduced into the adsorbent of the present invention is preferably not less than 0.01 µmol and not more than 30 µmol relative to 1 mL of the porous base matrix. The introduced quantity of affinity ligand is preferably not less than 0.01 µmol relative to 1 mL of the porous base matrix from the perspective of increasing the adsorbed quantity of purification target substance, and is preferably not more than 30 µmol from the perspective of limiting production costs. The introduced quantity of affinity ligand is more preferably not less than 0.03 µmol and not more than 3.6 µmol, further preferably not less than 0.75 µmol and not more than 1.8 µmol, particularly preferably not less than 0.1 µmol and not more than 0.9 µmol, and most preferably not less than 0.15 µmol and not more than 0.45 µmol, relative to 1 mL of the porous base matrix. The introduced quantity of affinity ligand can be obtained by measuring the absorbance from the affinity ligand in the supernatant of the reaction liquid after the immobilization reaction. In addition, the introduced quantity of affinity ligand can be obtained by elemental analysis. For example, in the case of an amino group-containing affinity ligand, it is possible to measure the introduced quantity of affinity ligand by subjecting the adsorbent to nitrogen content analysis. In addition, it is possible to obtain the quantity of ligand by quantitatively determining the quantity of amino groups by titration.

Affinity ligands used in medical adsorbents for treatment, adsorbents for purifying antibody drugs and the like are not particularly limited; but can be, for example, antigens or proteins having high specificity for an antibody, proteins G and L or variants thereof, or peptides having antibody binding activity. In particular, attention has been focused on adsorbents obtained by immobilizing protein A as an affinity ligand on a base matrix as adsorbents able to specifically adsorb and release immunoglobulin (IgG) and the like. Attention has been focused on adsorbents obtained by immobilizing protein A as adsorbents for the treatment of rheumatism, hemophilia and dilated cardiomyopathy. In addition, adsorbents that enable the purification of antibodies such as IgG to be carried out on a large scale, at high speed and at low cost are needed in the field of antibody drug purification. From the perspective, the adsorbent of the present invention is preferably one obtained by introducing protein A as an affinity ligand. The protein A able to be used in the present invention is not particularly limited, and it is possible to use a natural product or a genetically modified product without limitation. In addition, a protein that contains an antibody binding domain or a variant thereof or a fusion protein can be used as the protein A. In addition, it is possible to use a protein A produced from a bacterial extract or culture supernatant by combining and/or repeating purification methods selected from among chromatography methods such as ion exchange chromatography, hydrophobic interaction chromatography, gel filtration chromatography and hydroxyapatite chromatography and methods such as molecular weight fractionation and fractional precipitation that use membrane separation techniques. In particular, protein A obtained using the methods disclosed in PCT Publication No. WO 2006/004067 or U.S. Pat. No. 5,151,350 is preferred.

The method for introducing protein A as an affinity ligand into the porous base matrix can be one in which immobilization is carried out by reacting formyl group contained in the porous base matrix with amino group in the protein A, and such a method can be preferably used in the present invention.

For the adsorbent of the present invention, the concentration of the ligand leaked from the adsorbent into the target substance is preferably not more than 100 ppm. In the present invention, the concentration of the ligand leaked from the adsorbent into the target substance is defined as the ratio of the ligand to the target substance. When the concentration of the ligand leaked from the adsorbent into the target substance is not more than 100 ppm, it is possible to improve safety during treatment and purification, to further improve the purity of the target substance, and to reduce the complexity of subsequent steps in the purification. The concentration of the ligand leaked into the target substance is more preferably not less than 0 ppm and not more than 80 ppm, further preferably not less than 0 ppm and not more than 60 ppm, particularly preferably not less than 0 ppm and not more than 40 ppm, and most preferably not less than 0 ppm and not more than 20 ppm. The concentration of the ligand leaked into the target substance can be obtained using the method disclosed by Steindl F. et al., Journal of Immunological Methods, 235, (2000), pages 61-69.

In order to further reduce the quantity of the affinity ligand leaked in the adsorbent of the present invention, washing the adsorbent is preferred. The washing agent and washing method are not particularly limited, but stirring after passing or injecting a solution containing at least one of washing agent such as water, acetic acid, an alcohol, an organic solvent, a liquid having pH of 2-5, a liquid having pH of 8-13, sodium chloride, potassium chloride, sodium acetate, disodium hydrogen phosphate, sodium dihydrogen phosphate, a buffering agent, a surfactant, urea, guanidine, guanidine hydrochloride or another regenerant is preferred. In addition, it is preferable to use the washing agents alternately or repeatedly from the perspective of further reducing the quantity of ligand leaked.

The quantity of the target substance adsorbed onto the adsorbent of the present invention is preferably not less than 1 mg relative to 1 mL of the adsorbent. The quantity of the target substance adsorbed onto the adsorbent of the present invention is preferably not less than 1 mg relative to 1 mL of the adsorbent from the perspective of being able to carry out the purification efficiently. In addition, the quantity of the target substance adsorbed onto the adsorbent of the present invention is preferably not more than 1000 mg relative to 1 mL of the adsorbent from the perspective of the adsorbed target substance readily eluting from the adsorbent. The quantity of the target substance adsorbed onto the adsorbent is more preferably not less than 5 mg and not more than 500 mg, further preferably not less than 10 mg and not more than 250 mg, particularly preferably not less than 20 mg and not more than 150 mg, and most preferably not less than 30 mg and not more than 80 mg, relative to 1 mL of the adsorbent. The adsorbed quantity of the target substance can be obtained by bringing 0.5 mL of the adsorbent which is substituted with a pH 7.4 phosphate buffer manufactured by Sigma, into contact with a solution obtained by dissolving 70 mg of the target substance in 35 mL of a pH 7.4 phosphate buffer manufactured by Sigma, stirring at 25° C. for 2 hours, and then measuring reduction in the quantity of the target substance in the supernatant.

The volume average particle diameter of the adsorbent of the present invention is preferably not less than 20 μm and not more than 300 μm. The volume average particle diameter of the adsorbent is preferably not less than 20 μm from the perspective of preventing compaction, and is preferably not more than 300 μm from the perspective of increasing the adsorbed quantity of purification target substance when the porous base matrix is used as an adsorbent for purification. The volume average particle diameter of the adsorbent is more preferably not less than 40 μm and not more than 200 μm, further preferably not less than 60 μm and not more than 150 μm, and most preferably not less than 75 μm and not more than 100 μm.

The adsorbent of the present invention preferably has a compressive stress of not less than 0.006 MPa and not more than 1 MPa when compressed by 5%, a compressive stress of not less than 0.015 MPa and not more than 3 MPa when compressed by 10%, and a compressive stress of not less than 0.03 MPa and not more than 5 MPa when compressed by 15%.

As mentioned above, the adsorbent of the present invention can be produced by selecting an appropriate reaction each time from among a variety of affinity ligand immobilization reactions. When a protein is used as the affinity ligand, the reaction temperature is preferably 100° C. or less and higher than the melting point of the reaction liquid, more preferably 70° C. or less and higher than the melting point, further preferably 50° C. or less and higher than the melting point, particularly preferably 30° C. or less and higher than the melting point, and most preferably 15° C. or less and higher than the melting point, from the perspective of not causing the protein to lose activity.

When a protein is used as the affinity ligand, the pH of the reaction liquid is preferably not lower than 2 and lower than 13, more preferably not lower than 3 and lower than 12, further preferably not lower than 4 and not higher than 11, particularly preferably not lower than 5 and not higher than 11, and most preferably not lower than 6 and not higher than 11, from the perspective of not causing the protein to lose activity. However, from the perspective that the immobilized quantity of affinity ligand increases as the pH increases, the pH of the reaction liquid is preferably not lower than 7 and not higher than 11, more preferably not lower than 8 and not higher than 11, further preferably not lower than 9 and not higher than 11, and particularly preferably not lower than 10 and not higher than 11.

The method for charging the affinity ligand is not particularly limited, and the entire usage quantity thereof may be added at the start of the reaction, the divided quantities may be charged into multiple times and the reactions are repeated, the affinity ligand may be charged in small portions using an addition funnel and the like, or the porous base matrix may be charged in a reaction vessel in which the affinity ligand is charged.

The solvent to be used when the affinity ligand immobilization reaction is carried out is not particularly limited; but water, commonly used organic solvents such as heptane, dimethyl sulfoxide, dimethyl formamide and dioxolane, alcohols such as ethanol, methanol and propanol, or a mixed solvent of two or more thereof can be used.

It is preferable to add at least one of a carbonate, a citrate, an acetate, a phosphate and the like in order to increase the reaction efficiency, suppress fluctuations in pH and the like. The concentration of the salts in the reaction liquid is preferably not lower than 0.001 M and not higher than 10 M, more preferably not lower than 0.01 M and not higher than 5 M, further preferably not lower than 0.05 M and not higher than 1 M, and particularly preferably not less than 0.1 M and not higher than 0.5 M.

When a polymeric compound such as a protein is used as an affinity ligand, it is preferable to add a salt such as common salt in order to inhibit multi-point binding between the porous base matrix and the affinity ligand. The concentration of the salts such as common salt in the reaction liquid is preferably not lower than 0.001 M and not higher than 10 M, more preferably not lower than 0.01 M and not higher than 5 M, further preferably not lower than 0.05 M and not higher than 1 M, and particularly preferably not less than 0.1 M and not higher than 0.5 M.

When a formyl group-containing porous base matrix is used, it is preferable to stabilize the immobilization by adding a reducing agent such as sodium borohydride, trimethylamine borane, dimethylamine borane, picoline borane, pyridine borane, sodium cyanoborohydride or sodium triacetoxyborohydride after completion of the affinity ligand immobilization reaction, or by carrying out the immobilization reaction in the presence of such a reducing agent.

It is preferable to use a blocking agent after completion of the affinity ligand immobilization reaction in order to deactivate the active groups remaining on the porous base matrix. The blocking agent is not particularly limited, but a low molecular weight compound containing functional group that reacts with active group on the porous base matrix is preferred. It is preferable to use, for example, a low molecular weight compound containing amino group when the active group on the porous base matrix is epoxy group or formyl group. The example of such a low molecular weight compound is glycine, monoethanolamine, tris(hydroxymethyl) aminomethane and the like.

It is preferable that the affinity ligand immobilization reaction and related reactions such as the reduction reaction and blocking reaction is carried out under stirring or shaking; and the number of revolution or vibration per minute is not particularly limited, but is preferably not less than 1 rpm and not more than 1000 rpm, more preferably not less than 10 rpm and not more than 500 rpm, further preferably not less than 25 rpm and not more than 300 rpm, particularly preferably not less than 50 rpm and not more than 150 rpm, most preferably not less than 75 rpm and not more than 130 rpm, since uniform stirring is possible and for reasons such as not causing physical damage to the porous base matrix. It is particularly preferable to adjust the stirring rate according to the differences in the specific gravities of the raw materials and the strength of the porous base matrix.

The reaction time of the affinity ligand immobilization reaction is not particularly limited; but is preferably not less than 0.1 hours and not more than 1000 hours, more preferably not less than 0.5 hours and not more than 100 hours, further preferably not less than 1 hour and not more than 50 hours, particularly preferably not less than 1.5 hours and not more than 24 hours, most preferably not less than 3 hours and not more than 12 hours, from the perspectives of loss of activity of the affinity ligand and damage to the base matrix. It is more preferable to adjust the reaction time according to the reactivity, pH and reaction temperature.

The adsorbent of the present invention can be used in the purification of a target substance by affinity chromatography, in purification methods such as that disclosed in Non-patent Document 3 or in medical adsorbents for treatment. The purification methods and treatment methods are not particularly limited, and the adsorbent of the present invention can be suitably used in the methods disclosed in Non-patent Documents 1, 2 and 3 and other publicly known methods.

The adsorbent of the present invention enables the purification of a target substance on a large scale, at high speed and at low cost. Purification using the adsorbent of the present invention therefore preferably uses a column having a diameter of not less than 0.5 cm and a height of not less than 3 cm. When the diameter is not less than 0.5 cm and the height is not less than 3 cm, it is possible to carry out the purification or treatment efficiently. In addition, the column preferably has a diameter of not more than 2000 cm and a height of not more than 5000 cm, from the perspectives of precision and accuracy of the purification or treatment. The column more preferably has a diameter of not less than 2 cm and not more than 200 cm and a height of not less than 5 cm and not more than 300 cm, further preferably has a diameter of not less than 5 cm and not more than 100 cm and a height of not less than 8 cm and not more than 150 cm, particularly preferably has a diameter of not less than 10 cm and not more than 85 cm and a height of not less than 12 cm and not more than 85 cm, and most preferably has a diameter of not less than 20 cm and not more than 85 cm and a height of not less than 14 cm and not more than 35 cm.

Treatment or purification that uses the adsorbent of the present invention preferably has a step in which a liquid is passed at a linear speed of not less than 100 cm/h. It is preferable to have a step in which a liquid is passed at a linear speed of not less than 100 cm/h from the perspective of enabling the treatment or purification to be carried out efficiently. In addition, treatment or purification that uses the adsorbent of the present invention is preferably carried out at a linear speed of not more than 10000 cm/h from the perspectives of precision of the treatment or purification and durability of the apparatus. The linear speed during purification is more preferably not less than 150 cm/h and not more than 5000 cm/h, further preferably not less than 250 cm/h and not more than 2500 cm/h, particularly preferably not less than 500 cm/h and not more than 1500 cm/h, and most preferably not less than 700 cm/h and not more than 1200 cm/h.

The porous base matrix of the present invention, the adsorbent that uses the porous base matrix, production methods thereof, and treatment method and purification method that use the porous base matrix can carry out treatment or purification safely at high speed and can provide a purified product having high purity and safety in comparison with cases where the present invention is not used.

EXAMPLES

Examples of the present invention are now described, but the present invention is in no way limited by the examples. The volume of the porous base matrix means the natural settling volume unless otherwise specified. The natural settling volume is obtained by placing a slurry of the porous base matrix and RO water (water purified by reverse osmosis) in a weighing apparatus and allowing to stand for 2 hours in a vibration-free state. In addition, unless otherwise specified, the volume of the porous base matrix in the functional group content and the adsorbed quantity of IgG is the volume when a slurry of the porous base matrix and RO water is placed in a weighing apparatus and allowed to settle under vibration until the volume can be reduced no further.

Example 1

RO water was added to 75 mL of a porous cellulose base matrix having a volume average particle diameter of 92 μm, a resin content of 6% and an exclusion limit molecular weight of 50,000,000 (CK-A, manufactured by Chisso Corporation) to obtain a total volume of 95 mL. The mixture was placed in a plastic container (250 mL, manufactured by Sanplatec Co., Ltd.), and 27 mL of a 2M aqueous solution of sodium hydroxide (prepared from sodium hydroxide and RO water manufactured by Wako Pure Chemical Industries, Ltd.) was added thereto, and the mixture was heated at 40° C. for 30 minutes. After the temperature of the liquid reached 40° C., 9 mL of epichlorohydrin (manufactured by Wako Pure Chemical Industries, Ltd.) was added thereto, and the mixture was allowed to react at 40° C. for 2 hours while being shaken at 100 rpm using a constant temperature stirrer (thermostatic water bath T-25, manufactured by Thomas Kagaku Co., Ltd). After completion of the reaction, the porous base matrix was washed on a glass filter (26G-2 manufactured by TOP) with a volume of RO water equivalent to 20 times the volume of the porous base matrix so as to obtain an epoxidized porous base matrix. The obtained epoxidized porous base matrix (5.4 mL) was subjected to suction filtration, i.e. suction drying, on a glass filter (3G-2 manufactured by TOP) for 15 minutes, 1.5 g of the suction dried porous base matrix was weighed into a screw tube (manufactured by Maruemu Corporation) and 4.5 mL of a 1.3 M aqueous solution of sodium thiosulfate (prepared from sodium thiosulfate and RO water manufactured by Wako Pure Chemical Industries, Ltd.) was added thereto. After being heated at 45° C. for 30 minutes, the mixture was transferred to a 100 mL glass beaker together with 45 mL of RO water, and several drops of a 1% solution of phenolphthalein (prepared from phenolphthalein and ethanol manufactured by Wako Pure Chemical Industries, Ltd.) was added thereto. The epoxy group content was obtained by titrating with 0.01 N hydrochloric acid (for volumetric analysis, manufactured by Wako Pure Chemical Industries, Ltd.), and was found to be 14 μmol relative to 1 g of the suction dried porous base matrix.

Next, 54 mL of the epoxidized porous base matrix was substituted with 165 mL of a 0.5 M carbonate buffer having pH of 10 (prepared from sodium hydrogen carbonate and sodium carbonate and RO water manufactured by Wako Pure Chemical Industries, Ltd.). A 0.5 M carbonate buffer having pH of 10 was added to the substituted epoxidized porous base matrix to obtain a total volume of 108 mL. The mixture was placed in a plastic container (250 mL, manufactured by Sanplatec Co., Ltd.), and 0.51 g of D-(+)-glucosamine hydrochloride (manufactured by Wako Pure Chemical Industries, Ltd.) was further added thereto. The mixture was shaken at 50° C. for 4 hours at 100 rpm using a constant temperature stirrer (thermostatic water bath T-25, manufactured by Thomas Kagaku Co., Ltd), and then allowed to react by allowing to stand at room temperature for 12 hours. After the reaction, the porous base matrix was washed on a glass filter (26G-2 manufactured by TOP) with a volume of RO water equivalent to 20 times the volume of the porous base matrix so as to obtain a glucosaminated porous base matrix.

RO water was added to 25 mL of the obtained glucosaminated porous base matrix to obtain a total volume of 37 mL, and the mixture was then placed in a plastic container (100 mL, manufactured by Sanplatec Co., Ltd.). Next, 282 mg of sodium periodate (manufactured by Wako Pure Chemical Industries, Ltd.) was dissolved in 25 mL of RO water, and the aqueous sodium periodate solution was added to the plastic container. The mixture was allowed to react at 25° C. for 1 hour while being shaken at 100 rpm using a mixing rotor (variable mixing rotor VMR-5, manufactured by Iuchi Seieido Co., Ltd.) in an incubator (incubator LOW-TEMP ICB-151L, manufactured by Iwaki Glass Co., Ltd.). After the reaction, the porous base matrix was washed on a glass filter (26G-2 manufactured by TOP) with a volume of RO water equivalent to 20 times the volume of the porous base matrix so as to obtain a formyl group-containing porous base matrix. The formyl group content of the obtained formyl group-containing porous base matrix was measured using the method mentioned above, and was found to be 21 μmol relative to 1 mL of the porous base matrix.

The formyl group-containing porous base matrix (18.5 mL) was substituted with 56 mL of pH 10 buffer containing 0.5 M phosphoric acid and 0.15 M common salt buffer (prepared from disodium hydrogen phosphate, sodium chloride, sodium hydroxide and RO water manufactured by Wako Pure Chemical Industries, Ltd.) on a glass filter (17G-2 manufactured by TOP). A pH 10 buffer containing 0.5 M phosphoric acid and 0.15 M common salt was added to the substituted formyl group-containing porous base matrix to obtain a total volume of 30.7 mL. The mixture was placed in a plastic container (100 mL, manufactured by Sanplatec Co., Ltd.). To the mixture, 2.81 mL of a protein A-containing solution (PNXL28 manufactured by Kaneka Corporation) containing 52.6 mg/mL of protein A obtained using the method disclosed in PCT Publication No. WO 2006/004067 was added. The mixture was allowed to react at 4° C. for 12 hours while being shaken at 100 rpm using a mixing rotor (variable mixing rotor VMR-5, manufactured by Iuchi Seieido Co., Ltd.) in an incubator (incubator LOW-TEMP ICB-151L, manufactured by Iwaki Glass Co., Ltd.). The pH of the reaction liquid after the reaction was adjusted to 8 using 4 M hydrochloric acid (prepared from hydrochloric acid and RO water manufactured by Wako Pure Chemical Industries, Ltd.), and 52 mg of sodium borohydride was added thereto. The mixture was allowed to react under gentle shaking at 4° C. for 1 hour. After the reaction, the absorbance of the reaction liquid at the absorption maximum near 277 nm was measured; as a result, it was found that the introduced quantity of protein A affinity ligand was 6.6 mg relative to 1 mL of the porous base matrix.

After the reaction, the porous base matrix was washed on a glass filter (17G-2 manufactured by TOP) with a volume of RO water equivalent to 10 times the volume of the porous base matrix, and then substituted with a volume of 0.01 M hydrochloric acid (prepared from hydrochloric acid and RO water manufactured by Wako Pure Chemical Industries, Ltd.) equivalent to 3 times the volume of the porous base matrix. Next, 0.01 M hydrochloric acid was added to the substituted porous base matrix to obtain a total volume of 37 mL, and the mixture was placed in a plastic container (100 mL, manufactured by Sanplatec Co., Ltd.), and subjected to acid washing at room temperature for 30 minutes while being shaken at 100 rpm using a mixing rotor (variable mixing rotor VMR-5, manufactured by Iuchi Seieido Co., Ltd.). After the acid washing, the porous base matrix was washed on a glass filter (17G-2 manufactured by TOP) with a volume of RO water equivalent to 10 times the volume of the porous base matrix, and then substituted with a volume of an aqueous solution of 0.05 M sodium hydroxide and 1 M sodium sulfate (prepared from sodium hydroxide, sodium sulfate and RO water manufactured by Wako Pure Chemical Industries, Ltd.) equivalent to 3 times the volume of the porous base matrix.

Next, an aqueous solution of 0.05 M sodium hydroxide and 1 M sodium sulfate was added to the substituted porous base matrix to obtain a total volume of 37 mL, and the mixture was placed in a plastic container (100 mL, manufactured by Sanplatec Co., Ltd.). The mixture was subjected to alkali washing at room temperature for 20 minutes while being shaken at 100 rpm using a mixing rotor (variable mixing rotor VMR-5, manufactured by Iuchi Seieido Co., Ltd.). After the alkali washing, the porous base matrix was washed with RO water on a glass filter (17G-2 manufactured by TOP) until the electrical conductivity of the wash filtrate was 5 μS/cm or less so as to obtain the intended adsorbent, on which protein A was immobilized. The electrical conductivity of the wash filtrate was measured using an electrical conductivity meter (ECT-estr10 pure+, manufactured by Eutech Instruments). The quantity of IgG, which was the target substance, adsorbed on the obtained adsorbent was determined using the aforementioned method, and was found to be 44 mg relative to 1 mL of the adsorbent.

Example 2

It was possible to obtain an adsorbent by using a method similar to that in Example 1, except that fermented glucosamine K (manufactured by Kyowa Wellness Co., Ltd.) was used instead of D-(+)-glucosamine hydrochloride (manufactured by Wako Pure Chemical Industries, Ltd.).

Example 3

A slurry containing a porous cellulose base matrix having a volume average particle diameter of 92 μm, a resin content of 6% and an exclusion limit molecular weight of 50,000,000 (CK-A, manufactured by Chisso Corporation) and RO water at a ratio of 1:1 was subjected to suction filtration, i.e. suction drying, for 15 minutes on a glass filter (170-2 manufactured by TOP). The obtained suction dried porous cellulose base matrix (27.4 g) was placed in a plastic container (100 mL, manufactured by Sanplatec Co., Ltd.), and 27.4 mL of a 0.6 M aqueous solution of sodium hydroxide (prepared from sodium hydroxide and RO water manufactured by Wako Pure Chemical Industries, Ltd.) was added thereto, and the mixture was heated at 40° C. for 30 minutes. After the temperature of the liquid reached 40° C., 54.8 mg of sodium borohydride (manufactured by Wako Pure Chemical Industries, Ltd.) and then 27.4 mL of Denacol EX-314 (manufactured by Nagase ChemteX Corporation), which contains glycerol polyglycidyl ether as a crosslinking agent, were added thereto. The mixture was allowed to react at 40° C. for 5 hours under shaking at 100 rpm using a constant temperature stirrer (thermostatic water bath T-25, manufactured by Thomas Kagaku Co., Ltd). After completion of the reaction, the porous base matrix was washed on a glass filter (17G-2 manufactured by TOP) with a volume of RO water equivalent to 20 times the volume of the porous base matrix while being subjected to suction filtration so as to obtain a crosslinked porous base matrix. The compressive stress of the crosslinked porous base matrix was 0.020 MPa when compressed by 5%, 0.049 MPa when compressed by 10%, and 0.080 MPa when compressed by 15%.

RO water was added to the obtained crosslinked porous base matrix so as to obtain a volume which was twice that of the crosslinked porous base matrix. The mixture was placed in a glass beaker (300 mL), sealed with two sheets of aluminum foil, and then heated at 120° C. for 40 minutes using an autoclave (manufactured by Sakura). After being allowed to cool to room temperature, the porous base matrix was washed on a glass filter (17G-2 manufactured by TOP) with a volume of RO water equivalent to 5 times the volume of the porous base matrix so as to obtain a crosslinked porous base matrix in which the epoxy groups were converted into glyceryl groups. The washed crosslinked porous base matrix was subjected to a further crosslinking reaction using the same method. As a result, the compressive stress of the obtained crosslinked porous base matrix was 0.026 MPa when compressed by 5%, 0.063 MPa when compressed by 10%, and 0.103 MPa when compressed by 15%.

RO water was added to the crosslinked porous base matrix so as to obtain a volume which was twice that of the crosslinked porous base matrix. The mixture was placed in a glass beaker (300 mL), sealed with two sheets of aluminum foil, and then heated at 120° C. for 40 minutes using an autoclave (manufactured by Sakura). After being allowed to cool to room temperature, the porous base matrix was washed on a glass filter (17G-2 manufactured by TOP) with a volume of RO water equivalent to 5 times the volume of the porous base matrix so as to obtain a crosslinked porous base matrix-A, in which the epoxy groups were converted into glyceryl groups.

RO water was added to 10 mL of the washed crosslinked porous base matrix to obtain a total volume of 12.6 mL. The mixture was placed in a centrifuging tube (50 mL, manufactured by Iwaki Glass Co., Ltd.), and 3.7 mL of a 2 M aqueous solution of sodium hydroxide (prepared from sodium hydroxide and RO water manufactured by Wako Pure Chemical Industries, Ltd.) was added thereto. The mixture was heated at 40° C. for 30 minutes. After the temperature of the liquid reached 40° C., 1.3 mL of epichlorohydrin (manufactured by Wako Pure Chemical Industries, Ltd.) was added thereto. The mixture was allowed to react at 40° C. for 2 hours while being shaken at 100 rpm using a constant temperature stirrer (thermostatic water bath T-25, manufactured by Thomas Kagaku Co., Ltd.). After completion of the reaction, the porous base matrix was washed on a glass filter (17G-2 manufactured by TOP) with a volume of RO water equivalent to 20 times the volume of the porous base matrix so as to obtain an epoxidized porous base matrix.

Next, 10 mL of the epoxidized porous base matrix was substituted with 30 mL of a 0.5 M carbonate buffer having pH of 10 (prepared from sodium hydrogen carbonate, sodium carbonate and RO water manufactured by Wako Pure Chemical Industries, Ltd.) on a glass filter (17G-2 manufactured by TOP). A 0.5 M carbonate buffer having pH of 10 was added to the substituted epoxidized porous base matrix to obtain a total volume of 20 mL. The mixture was placed in a centrifuging tube (50 mL, manufactured by Iwaki Glass Co., Ltd.), and 95 mg of D-(+)-glucosamine hydrochloride (manufactured by Wako Pure Chemical Industries, Ltd.) was further added thereto. The mixture was shaken at 50° C. for 4 hours at 100 rpm using a constant temperature stirrer (thermostatic water bath T-25, manufactured by Thomas Kagaku Co., Ltd), and then allowed to react by allowing to stand at room temperature for 12 hours. After the reaction, the porous base matrix was washed on a glass filter (17G-2 manufactured by TOP) with a volume of RO water equivalent to 20 times the volume of the porous base matrix so as to obtain a glucosaminated porous base matrix.

RO water was added to 8.5 mL of the obtained glucosaminated porous base matrix to obtain a total volume of 12.8 mL, and the mixture was then placed in a centrifuging tube (50 mL, manufactured by Iwaki Glass Co., Ltd.). Next, 98 mg of sodium periodate (manufactured by Wako Pure Chemical Industries, Ltd.) was dissolved in 8.5 mL of RO water, and the aqueous sodium periodate solution was added to the centrifuging tube. The mixture was allowed to react at 25° C. for 1 hour while being shaken at 100 rpm using a mixing rotor (variable mixing rotor VMR-5, manufactured by Iuchi Seieido Co., Ltd.) in an incubator (incubator LOW-TEMP ICB-151L, manufactured by Iwaki Glass Co., Ltd.). After the reaction, the porous base matrix was washed on a glass filter (17G-2 manufactured by TOP) with a volume of RO water equivalent to 20 times the volume of the porous base matrix so as to obtain a formyl group-containing porous base matrix. The formyl group content of the obtained formyl group-containing porous base matrix was measured using the method mentioned above, and was found to be 56 μmol relative to 1 mL of the porous base matrix.

The formyl group-containing porous base matrix (7.4 mL) was substituted with 30 mL of a pH 10 buffer containing 0.5 M phosphoric acid and 0.15 M common salt (prepared from disodium hydrogen phosphate, sodium chloride, sodium hydroxide and RO water manufactured by Wako Pure Chemical Industries, Ltd.) on a glass filter (17G-2, manufactured by TOP). A pH 10 buffer containing 0.5 M phosphoric acid and 0.15 M common salt was added to the substituted formyl group-containing porous base matrix to obtain a total volume of 12.3 mL. The mixture was placed in a centrifuging tube (50 mL, manufactured by Iwaki Glass Co., Ltd.), and 1.13 mL of a protein A-containing solution (PNXL28 manufactured by Kaneka Corporation) containing 52.6 mg/mL of protein A obtained using the method disclosed in PCT Publication No. WO 2006/004067 was added thereto. The mixture was allowed to react at 4° C. for 12 hours while being shaken at 100 rpm using a mixing rotor (variable mixing rotor VMR-5, manufactured by Iuchi Seieido Co., Ltd.) in an incubator (incubator LOW-TEMP ICB-151L, manufactured by Iwaki Glass Co., Ltd.). The pH of the reaction liquid after the reaction was adjusted to 8 using 4 M hydrochloric acid (prepared from hydrochloric acid and RO water manufactured by Wako Pure Chemical Industries, Ltd.), and 21 mg of sodium borohydride was added thereto. The mixture was allowed to react under gentle shaking at 4° C. for 1 hour. After the reaction, the absorbance of the reaction liquid at the absorption maximum near 277 nm was measured; as a result, it was found that the introduced quantity of protein A affinity ligand was 8 mg relative to 1 mL of the porous base matrix.

After the reaction, the porous base matrix was subjected to the same acid washing, alkali washing and RO water washing as in Example 1 so as to obtain the intended adsorbent, on which protein A was immobilized. The quantity of IgG, which was the target substance, adsorbed on the obtained adsorbent was determined using the aforementioned method, and was found to be 26 mg relative to 1 mL of the adsorbent.

In addition, the compressive stress of the obtained adsorbent was 0.053 MPa when compressed by 5%, not less than 0.110 MPa when compressed by 10%, and not less than 0.110 MPa when compressed by 15%.

Example 4

A crosslinked porous base matrix was obtained using a method similar to that in Example 3, except that Denacol EX-421 (manufactured by Nagase ChemteX Corporation), which contains diglycerol polyglycidyl ether, was used as a crosslinking agent. The compressive stress of the crosslinked porous base matrix obtained from the first crosslinking reaction was 0.018 MPa when compressed by 5%, 0.046 MPa when compressed by 10%, and 0.075 MPa when compressed by 15%. The compressive stress of the crosslinked porous base matrix obtained from the second crosslinking reaction was 0.021 MPa when compressed by 5%, 0.055 MPa when compressed by 10%, and 0.095 MPa when compressed by 15%.

Furthermore, using a method similar to that in Example 3, a glucosaminated porous base matrix was obtained, and a formyl group-containing porous base matrix having a formyl group content of 58 µmol relative to 1 mL of the porous base matrix was then obtained. Next, using a method similar to that in Example 3, an adsorbent was obtained in which the introduced quantity of the protein A affinity ligand was 8 mg relative to 1 mL of the porous base matrix and the adsorbed quantity of IgG, which was the target substance, was 25 mg relative to 1 mL of the adsorbent. In addition, the compressive stress of the obtained adsorbent was 0.039 MPa when compressed by 5%, 0.085 MPa when compressed by 10%, and not less than 0.110 MPa when compressed by 15%.

Example 5

A crosslinked porous base matrix-A was obtained using a method similar to that in Example 3. In order to treat the glyceryl group of the crosslinked porous base matrix-A, RO water was added to 25.5 mL of the crosslinked porous base matrix-A to obtain a total volume of 38.3 mL. The mixture was placed in a plastic container (100 mL, manufactured by Sanplatec Co., Ltd.), and 25.5 mL of a solution obtained by dissolving 293 mg of sodium periodate (manufactured by Wako Pure Chemical Industries, Ltd.) was added thereto, and allowed to react at 25° C. for 1 hour while being shaken at 100 rpm using a mixing rotor (variable mixing rotor VMR-5, manufactured by Iuchi Seieido Co., Ltd.) in an incubator (incubator LOW-TEMP ICB-151L, manufactured by Iwaki Glass Co., Ltd.). After the reaction, the porous base matrix was washed on a glass filter (17G-2 manufactured by TOP) with a volume of RO water equivalent to 20 times the volume of the porous base matrix.

Next, RO water was added to 25 mL of the obtained porous base matrix to obtain a total volume of 37.5 mL. The mixture was placed in a plastic container (100 mL, manufactured by Sanplatec Co., Ltd.), and 25 mL of a solution obtained by dissolving 72 mg of sodium periodate (manufactured by Wako Pure Chemical Industries, Ltd.) was added thereto. The mixture was allowed to react at 25° C. for 1 hour while being shaken at 100 rpm using a mixing rotor (variable mixing rotor VMR-5, manufactured by Iuchi Seieido Co., Ltd.) in an incubator (incubator LOW-TEMP ICB-151L, manufactured by Iwaki Glass Co., Ltd.). After the reaction, the porous base matrix was washed on a glass filter (17G-2 manufactured by TOP) with a volume of RO water equivalent to 20 times the volume of the porous base matrix so as to obtain a crosslinked porous base matrix-B in which the glyceryl group was treated. The formyl group content of the crosslinked porous base matrix-B was 65 µmol relative to 1 mL of the porous base matrix.

The crosslinked porous base matrix-B (11.4 mL) was substituted with 35 mL of a 0.25 M phosphate buffer having pH of 10 (prepared using disodium hydrogen phosphate, sodium hydroxide and RO water manufactured by Wako Pure Chemical Industries, Ltd.) on a glass filter (17G-2 manufactured by TOP). The same buffer as that used in the substitution was added to the substituted crosslinked porous base matrix-B to obtain a total volume of 22.8 mL. The mixture was placed in a centrifuging tube (50 mL, manufactured by Iwaki Glass Co., Ltd.), and fermented glucosamine K (manufactured by Kyowa Hakko Kogyo Co., Ltd.) was added thereto in a quantity equivalent to 10 times the molar quantity of the formyl group content of the porous base matrix-B. The mixture was shaken at 50° C. for 5 hours at 100 rpm using a constant temperature stirrer (thermostatic water bath T-25, manufactured by Thomas Kagaku Co., Ltd). Next, after the mixture was allowed to cool to room temperature, 65 mg of sodium borohydride (manufactured by Wako Pure Chemical Industries, Ltd.) was added thereto, and the mixture was allowed to react for 1 hour while being gently stirred. After the reaction, the porous base matrix was washed with a volume of RO water equivalent to 20 times the volume of the porous base matrix so as to obtain a glucosaminated porous base matrix. The introduced quantity of glucosamine into the porous base matrix was 33 µmol relative to 1 mL of the porous base matrix.

The glucosaminated porous base matrix was subjected to formylation using a method similar to that in Example 1 so as to obtain a formyl group-containing porous base matrix in which the formyl group content was 23 µmol relative to 1 mL of the porous base matrix. Next, protein A was immobilized, and washing was carried out using methods similar to those in Example 1 so as to obtain an adsorbent in which 6.3 mg of protein A was immobilized relative to 1 mL of porous base matrix. The quantity of IgG, which was the target substance, adsorbed on the obtained adsorbent was determined using the aforementioned method, and was found to be 45 mg relative to 1 mL of the adsorbent.

Example 6

RO water was added to 12.5 mL of the porous base matrix-B obtained in Example 5 to obtain a total volume of 25 mL. The mixture was placed in a centrifuging tube (50 mL, manufactured by Iwaki Glass Co., Ltd.), and 71 mg of sodium borohydride (manufactured by Wako Pure Chemical Industries, Ltd.) was then added thereto. The mixture was allowed to react at room temperature for 1 hour while being gently stirred. After the reaction, the porous base matrix was washed on a glass filter (17G-2 manufactured by TOP) with a volume of RO water equivalent to 20 times the volume of the porous base matrix so as to obtain a crosslinked porous base matrix-C in which the formyl group was converted to hydroxy group. The crosslinked porous base matrix-C was used as a staring base matrix, and epoxy group was introduced using a method similar to that in Example 1 so as to obtain a crosslinked porous base matrix-D. A glucosaminated porous base matrix was obtained using a method similar to that in Example 1, except that a 0.7 M aqueous solution of sodium hydroxide (prepared from sodium hydroxide and RO water manufactured by Wako Pure Chemical Industries, Ltd.) was used instead of carbonate buffer, and fermented glucosamine K (manufactured by Kyowa Hakko Kogyo Co., Ltd.) was used instead of D-(+)-glucosamine hydrochloride (manufactured by Wako Pure Chemical Industries, Ltd.), and the reaction was carried out for 5 hours at 50° C. and then overnight at room temperature. The glucosaminated porous base matrix was subjected to formylation using a method similar to that in Example 1 so as to obtain a formyl group-containing porous base matrix in which the formyl group content was 7.6 μmol relative to 1 mL of the porous base matrix. Next, protein A was immobilized, and washing was carried out using methods similar to those in Example 1 so as to obtain an adsorbent in which 5.3 mg of protein A was immobilized relative to 1 mL of porous base matrix. The quantity of IgG, which was the target substance, adsorbed on the obtained adsorbent was determined using the aforementioned method, and was found to be 48 mg relative to 1 mL of the adsorbent.

Example 7

An epoxidized porous base matrix was obtained using a method similar to that in Example 1, and a glucosaminated porous base matrix was then obtained using a method similar to that in Example 6, except that a 0.7 M aqueous solution of sodium hydroxide (prepared from sodium hydroxide and RO water manufactured by Wako Pure Chemical Industries, Ltd.) was used instead of carbonate buffer and fermented glucosamine K (manufactured by Kyowa Hakko Kogyo Co., Ltd.) was used instead of D-(+)-glucosamine hydrochloride (manufactured by Wako Pure Chemical Industries, Ltd.). The glucosaminated porous base matrix was used, and a formyl group-containing porous base matrix and adsorbent were obtained using methods similar to those in Example 1.

Example 8

A formyl group-containing porous base matrix and adsorbent were obtained using methods similar to those in Example 6, except that a 0.007 M aqueous solution of sodium hydroxide (prepared from sodium hydroxide and RO water manufactured by Wako Pure Chemical Industries, Ltd.) was used instead of 0.7 M aqueous solution of sodium hydroxide.

Example 9

A formyl group-containing porous base matrix and adsorbent were obtained using methods similar to those in Example 6, except that a 0.5 M carbonate buffer having pH of 10 (prepared from sodium hydrogen carbonate, sodium carbonate and RO water manufactured by Wako Pure Chemical Industries, Ltd.) was used instead of 0.7 M aqueous solution of sodium hydroxide.

Example 10

A formyl group-containing porous base matrix and adsorbent were obtained using methods similar to those in Example 5, except that a 0.007 M aqueous solution of sodium hydroxide (prepared from sodium hydroxide and RO water manufactured by Wako Pure Chemical Industries, Ltd.) was used as the solvent for the glucosamine introduction instead of 0.25 M phosphate buffer having pH of 10.

Example 11

An adsorbent was obtained using a method similar to that in Example 5, except that the pH of the buffer in the protein A immobilization reaction was changed from 10 to 11.

Example 12

An adsorbent was obtained using a method similar to that in Example 6, except that the pH of the buffer in the protein A immobilization reaction was changed from 10 to 11.

Example 13

An adsorbent was obtained using a method similar to that in Example 10, except that the pH of the buffer in the protein A immobilization reaction was changed from 10 to 11.

Example 14

A crosslinked porous base matrix-A (500 mL) was obtained using a method similar to that in Example 3. The porous base matrix-A was subjected to wet classification for 2 hours using a 90 μm mesh (wire diameter: 63 μm, manufactured by Nonaka Rikaki) and a classifier (300-MM, manufactured by Tsutsui Scientific Instruments Co., Ltd.) so as to obtain a porous base matrix-D having volume average particle diameter of 83 μm. A glucosaminated porous base matrix in which the immobilized quantity of glucosamine was 20 μmol relative to 1 mL of the porous base matrix was obtained using a method similar to that in Example 5, except that the porous base matrix-D was used, the pH after the reaction was adjusted to 10 by using a 4 N aqueous solution of sodium hydroxide immediately after adding the fermented glucosamine K, and the glucosamination reaction was carried out at 4° C. Next, using the glucosaminated porous base matrix, a formyl group-containing porous base matrix was obtained using a method similar to that in Example 5. Next, an adsorbent on which protein A was immobilized was obtained using a method similar to that in Example 5, except that the buffer to be used was changed to a 0.5 M phosphate and 0.15 M common salt buffer having pH of 11. The quantity of protein A immobilized on the adsorbent was 7.5 mg relative to 1 mL of the adsorbent. The quantity of IgG, which was the target substance, adsorbed on the obtained adsorbent was determined using the aforementioned method, and was found to be 51 mg relative to 1 mL of the adsorbent.

Example 15

A formyl group-containing porous base matrix and then an adsorbent on which protein A was immobilized were obtained using methods similar to those in Example 14, except that the porous base matrix-A was used instead of porous base matrix-D.

Example 16

A formyl group-containing porous base matrix and then an adsorbent on which protein A was immobilized were obtained using methods similar to those in Example 14, except that a porous base matrix-E, obtained by blending porous base matrix-A and porous base matrix-D so that the volume average particle diameter thereof was 86 μm, was used instead of porous base matrix-D.

Example 17

A glucosaminated porous base matrix was obtained, a formyl group-containing porous base matrix was then obtained and an adsorbent on which protein A was immobilized was then obtained, using methods similar to those in Example 14, except that the pH of the reaction liquid was adjusted to 8 using a 4 N aqueous solution of sodium hydroxide immediately after adding fermented glucosamine K. The quantity of IgG, which was the target substance, adsorbed on the obtained adsorbent was determined using the aforementioned method, and was found to be 49 mg relative to 1 mL of the adsorbent.

Example 18

A formyl group-containing porous base matrix and then an adsorbent on which protein A was immobilized were obtained, using methods similar to those in Example 17, except that the porous base matrix-A was used instead of porous base matrix-D.

Example 19

A formyl group-containing porous base matrix and then an adsorbent on which protein A was immobilized were obtained, using methods similar to those in Example 18, except that a porous base matrix-E, obtained by blending porous base matrix-A and porous base matrix-D so that the volume average particle diameter thereof was 86 µm, was used instead of porous base matrix-D.

Example 20

A formyl group-containing porous base matrix and an adsorbent on which protein A was immobilized were then obtained, using methods similar to those in Example 15, except that a glucosaminated porous base matrix was obtained using a method similar to that in Example 17, and the concentration of sodium periodate in the added aqueous solution of sodium periodate was half that in Example 15. The quantity of IgG, which was the target substance, adsorbed on the obtained adsorbent was determined using the aforementioned method, and was found to be 51 mg relative to 1 mL of the adsorbent.

Comparative Example 1

RO water was added to 175 mL of a porous cellulose base matrix having a volume average particle diameter of 92 µm, a resin content of 6% and an exclusion limit molecular weight of 50,000,000 (CK-A, manufactured by Chisso Corporation) to obtain a total volume of 221 mL. The mixture was placed in a plastic container (500 mL, manufactured by Sanplatec Co., Ltd.), and 64 mL of a 2 M aqueous solution of sodium hydroxide (prepared from sodium hydroxide and RO water manufactured by Wako Pure Chemical Industries, Ltd.) was added thereto, and the mixture was heated at 40° C. for 30 minutes. After the temperature of the liquid reached 40° C., 11 mL of epichlorohydrin (manufactured by Wako Pure Chemical Industries, Ltd.) was added thereto, and the mixture was allowed to react at 40° C. for 2 hours while being shaken at 100 rpm using a constant temperature stirrer (thermostatic water bath T-25, manufactured by Thomas Kagaku Co., Ltd). After completion of the reaction, the porous base matrix was washed on a glass filter (26G-2 manufactured by TOP) with a volume of RO water equivalent to 20 times the volume of the porous base matrix so as to obtain an epoxidized porous base matrix.

The obtained epoxidized porous base matrix (5.4 mL) was subjected to suction filtration, i.e. suction drying, on a glass filter (3G-2 manufactured by TOP) for 15 minutes, 1.5 g of the suction dried porous base matrix was weighed into a screw tube (manufactured by Maruemu Corporation), and 4.5 mL of a 1.3 M aqueous solution of sodium thiosulfate (prepared from sodium thiosulfate and RO water manufactured by Wako Pure Chemical Industries, Ltd.) was added thereto. After being heated at 45° C. for 30 minutes, the mixture was transferred to a 100 mL glass beaker together with 45 mL of RO water, and several drops of a 1% solution of phenolphthalein (prepared from phenolphthalein and ethanol manufactured by Wako Pure Chemical Industries, Ltd.) were added thereto. The epoxy group content was obtained by titrating with 0.01 N hydrochloric acid (for volumetric analysis, manufactured by Wako Pure Chemical Industries, Ltd.), and was found to be 7 µmol relative to 1 g of the suction dried porous base matrix.

Next, RO water was added to the obtained epoxidized porous base matrix so as to obtain a volume which was twice that of the crosslinked porous base matrix. The mixture was placed in a 1 L glass beaker, sealed with two sheets of aluminum foil and then heated at 120° C. for 40 minutes using an autoclave (manufactured by Sakura). After the mixture was allowed to cool to room temperature, the porous base matrix was washed on a glass filter (17G-2 manufactured by TOP) with a volume of RO water equivalent to 5 times the volume of the porous base matrix so as to obtain a porous base matrix in which the epoxy group was converted into glyceryl group.

RO water was added to 83 mL of the washed porous base matrix to obtain a total volume of 125 mL, and the mixture was then placed in a plastic container (500 mL, manufactured by Sanplatec Co., Ltd.). Next, 119 mg of sodium periodate (manufactured by Wako Pure Chemical Industries, Ltd.) was dissolved in 83 mL of RO water, and the aqueous sodium periodate solution was added to the plastic container, and the mixture was allowed to react at 25° C. for 1 hour while being shaken at 100 rpm using a mixing rotor (variable mixing rotor VMR-5, manufactured by Iuchi Seieido Co., Ltd.) in an incubator (incubator LOW-TEMP ICB-151L, manufactured by Iwaki Glass Co., Ltd.). After the reaction, the porous base matrix was washed on a glass filter (26G-2 manufactured by TOP) with a volume of RO water equivalent to 20 times the volume of the porous base matrix so as to obtain a formyl group-containing porous base matrix. The formyl group content of the obtained formyl group-containing porous base matrix was measured using the method mentioned above, and was found to be 7 µmol relative to 1 mL of the porous base matrix.

The formyl group-containing porous base matrix (21 mL) was substituted with 63 mL of a pH 10 buffer containing 0.5 M phosphoric acid and 0.15 M common salt (prepared from disodium hydrogen phosphate, sodium chloride, sodium hydroxide and RO water manufactured by Wako Pure Chemical Industries, Ltd.) on a glass filter (17G-2, manufactured by TOP). A pH 10 buffer containing 0.5 M phosphoric acid and 0.15 M common salt was added to the substituted formyl group-containing porous base matrix to obtain a total volume of 35 mL. The mixture was placed in a plastic container (100 mL, manufactured by Sanplatec Co., Ltd.), and 3.16 mL of a protein A-containing solution (PNXL28 manufactured by Kaneka Corporation) containing 52.6 mg/mL of protein A obtained using the method disclosed in PCT Publication No. WO 2006/004067 was added thereto. The mixture was allowed to react at 4° C. for 12 hours while being shaken at 100 rpm using a mixing rotor (variable mixing rotor VMR-5, manufactured by Iuchi Seieido Co., Ltd.) in an incubator (incubator LOW-TEMP ICB-151L, manufactured by Iwaki Glass Co., Ltd.). The pH of the reaction liquid after the reaction was adjusted to 8 using 4 M hydrochloric acid (prepared from hydrochloric acid and RO water manufactured by Wako Pure Chemical Industries, Ltd.), and 52 mg of sodium borohydride was added thereto, and the mixture was allowed to react under gentle shaking at 4° C. for 1 hour. After the reaction, the absorbance of the reaction liquid at the absorption maximum near 277 nm was measured; as a result, it was found that the introduced quantity of protein A affinity ligand was 5.3 mg relative to 1 mL of the porous base matrix.

After the reaction, the porous base matrix was washed on a glass filter (25G-2 manufactured by TOP) with a volume of RO water equivalent to 20 times the volume of the porous base matrix, and RO water was added to the porous base matrix so as to obtain a volume which was twice that of the porous base matrix. The mixture was placed in a plastic container (100 mL, manufactured by Sanplatec Co., Ltd.). Next, 3.26 g of sodium borohydride was dissolved in RO water to obtain a volume of 21 mL, and the total quantity of the solution was added to the plastic container gradually over a period of 5 hours. After the reaction, the porous base matrix was subjected to the same acid washing, alkali washing and RO water washing as in Example 1 so as to obtain the intended adsorbent, on which protein A was immobilized.

The quantity of IgG, which was the target substance, adsorbed on the obtained adsorbent was determined using the aforementioned method, and was found to be 46 mg relative to 1 mL of the adsorbent.

Example 21

A porous cellulose base matrix (CK-C manufactured by Chisso Corporation) having a volume average particle diameter of 97 μm and a resin content of 10% was classified using a 90 μm mesh (manufactured by Nonaka Rikaki) so as to obtain a porous cellulose base matrix having a volume average particle diameter of 85 μm. RO water was added to 362 mL of the base matrix to obtain a total volume of 489 mL. The mixture was placed in a separable flask, and the flask was placed in a constant temperature stirrer (thermostatic water bath T-25, manufactured by Thomas Kagaku Co., Ltd.) at 25° C. Next, sodium periodate (manufactured by Wako Pure Chemical Industries, Ltd.) was dissolved in RO water so as to obtain a solution containing 11.45 mg/ml of sodium periodate, and 362 mL of the solution was added to the separable flask, and the mixture was stirred at 150 rpm for 1 hour at 25° C. (the used stirrer was a Mazela Z). After the reaction, the porous base matrix was washed on a glass filter (26G-2 manufactured by TOP) with a volume of RO water equivalent to 20 times the volume of the porous base matrix so as to obtain a formyl group-containing porous base matrix.

The formyl group content of the obtained formyl group-containing porous base matrix was measured using the method mentioned above, and was found to be 16 μmol relative to 1 mL of the porous base matrix. In addition, the compressive stress of the base matrix was 0.009 MPa when compressed by 5%, 0.026 MPa when compressed by 10%, and 0.049 MPa when compressed by 15%. In addition, the volume average particle diameter of the base matrix was 84 μm.

The formyl group-containing porous base matrix (315 mL) was substituted with 1500 mL of pH 11 buffer containing 0.5 M phosphoric acid and 0.15 M common salt (prepared from disodium hydrogen phosphate, sodium chloride, sodium hydroxide and RO water manufactured by Wako Pure Chemical Industries, Ltd.) on a glass filter (26G-2, manufactured by TOP). A pH 10 buffer containing 0.5 M phosphoric acid and 0.15M common salt was added to the substituted formyl group-containing porous base matrix to obtain a total volume of 522 mL. The mixture was placed in a separable flask, and 48.84 mL of a protein A-containing solution (PNXL29 manufactured by Kaneka Corporation) containing 51.6 mg/mL of protein A obtained using the method disclosed in PCT Publication No. WO 2006/004067 was added thereto. The mixture was allowed to react at 4° C. for 12 hours while being stirred (the used stirrer was a Mazela Z) in an incubator (incubator LOW-TEMP ICB-151L, manufactured by Iwaki Glass Co., Ltd.). The pH of the reaction liquid after the reaction was adjusted to 8 using 4 M hydrochloric acid (prepared from hydrochloric acid and RO water manufactured by Wako Pure Chemical Industries, Ltd.), and 0.89 g of sodium borohydride (manufactured by Wako Pure Chemical Industries, Ltd.) was added thereto. The mixture was allowed to react under gentle stirring at 4° C. for 1 hour. After the reaction, the absorbance of the reaction liquid at the absorption maximum near 276 nm was measured; as a result, it was found that the introduced quantity of protein A affinity ligand was 4.6 mg relative to 1 mL of the porous base matrix.

After the reaction, the porous base matrix was washed on a glass filter (26G-2 manufactured by TOP) with a volume of RO water equivalent to 10 times the volume of the porous base matrix, and then was substituted with a volume of 0.01 M hydrochloric acid (prepared from hydrochloric acid and RO water manufactured by Wako Pure Chemical Industries, Ltd.) equivalent to 3 times the volume of the porous base matrix. Next, 0.01 M hydrochloric acid was added to the substituted porous base matrix to obtain a total volume of 630 mL. The mixture was placed in a separable flask, and the porous base matrix was subjected to acid washing at room temperature for 30 minutes under stirring. After the acid washing, the porous base matrix was washed on a glass filter (26G-2 manufactured by TOP) with a volume of RO water equivalent to 10 times the volume of the porous base matrix, and then was substituted with a volume of an aqueous solution of 0.05 M sodium hydroxide and 1 M sodium sulfate (prepared from sodium hydroxide, sodium sulfate and RO water manufactured by Wako Pure Chemical Industries, Ltd.) equivalent to 3 times the volume of the porous base matrix. Next, an aqueous solution containing 0.05 M sodium hydroxide and 1M sodium sulfate was added to the substituted porous base matrix to obtain a total volume of 630 mL. The mixture was placed in a separable flask, and the porous base matrix was subjected to alkali washing at room temperature for 20 minutes under stirring. After the alkali washing, the porous base matrix was washed with RO water on a glass filter (26G-2 manufactured by TOP) until the electrical conductivity of the wash filtrate was 5 μS/cm or less so as to obtain the intended adsorbent, on which protein A was immobilized.

The electrical conductivity of the wash filtrate was measured using an electrical conductivity meter (ECTestr10 pure+ manufactured by Eutech Instruments). The quantity of IgG, which was the purification target substance, adsorbed on the obtained adsorbent was determined using the aforementioned method, and was found to be 55 mg relative to 1 mL of the adsorbent.

The compressive stress of the obtained adsorbent was 0.008 MPa when compressed by 5%, 0.023 MPa when compressed by 10%, and not less than 0.042 MPa when compressed by 15%. In addition, the volume average particle diameter of the adsorbent was 86 μm.

Example 22

RO water was added to 27.5 mL of a porous cellulose base matrix (CK-C manufactured by Chisso Corporation) having an average particle diameter of 97 μm and a resin content of 10% to obtain a total volume of 41.25 mL. The total volume of the mixture was transferred to a 100 mL plastic container.

Next, sodium periodate (manufactured by Wako Pure Chemical Industries, Ltd.) was dissolved in RO water to obtain a solution containing 11.45 mg/mL of sodium periodate, and 27.5 mL of the aqueous sodium periodate solution was added to the plastic container. The mixture was allowed to react at 25° C. for 1 hour while being shaken at 100 rpm using a mixing rotor (variable mixing rotor VMR-5, manufactured by Iuchi Seieido Co., Ltd.) in an incubator (incubator LOW-TEMP ICB-151L, manufactured by Iwaki Glass Co., Ltd.). After the reaction, the porous base matrix was washed on a glass filter with a volume of RO water equivalent to 20 times the volume of the porous base matrix so as to obtain a formyl group-containing porous base matrix.

The formyl group content of the obtained formyl group-containing porous base matrix was measured using the method mentioned above, and was found to be 15 μmol relative to 1 mL of the porous base matrix. In addition, the compressive stress of the base matrix was 0.012 MPa when compressed by 5%, 0.029 MPa when compressed by 10%, and 0.052 MPa when compressed by 15%. In addition, the volume average particle diameter of the base matrix was 100 μm.

The formyl group-containing porous base matrix (25 mL) was substituted with 125 mL of a pH 11 buffer containing 0.5 M phosphoric acid and 0.15 M common salt (prepared from disodium hydrogen phosphate, sodium chloride, sodium hydroxide and RO water manufactured by Wako Pure Chemical Industries, Ltd.) on a glass filter (17G-2 manufactured by TOP). A pH 11 buffer containing 0.5 M phosphoric acid and 0.15 M common salt was added to the substituted formyl group-containing porous base matrix to obtain a total volume of 41.5 mL. The mixture was placed in a plastic container (100 mL, manufactured by Sanplatec Co., Ltd.), and 3.80 mL of a protein A-containing solution (PNXL28 manufactured by Kaneka Corporation) containing 52.6 mg/mL of protein A obtained using the method disclosed in PCT Publication No. WO 2006/004067 was added thereto. The mixture was allowed to react at 4° C. for 12 hours while being shaken at 100 rpm using a mixing rotor (variable mixing rotor VMR-5, manufactured by Iuchi Seieido Co., Ltd.) in an incubator (incubator LOW-TEMP ICB-151L, manufactured by Iwaki Glass Co., Ltd.). The pH of the reaction liquid after the reaction was adjusted to 8 using 4 M hydrochloric acid (prepared from hydrochloric acid and RO water manufactured by Wako Pure Chemical Industries, Ltd.), and 0.071 g of sodium borohydride (manufactured by Wako Pure Chemical Industries, Ltd.) was added thereto. The mixture was allowed to react under gentle stirring at 4° C. for 1 hour. After the reaction, the absorbance of the reaction liquid at the absorption maximum near 276 nm was measured; as a result, it was found that the introduced quantity of protein A affinity ligand was 4.0 mg relative to 1 mL of the porous base matrix. After the reaction, the porous base matrix was subjected to the same acid washing, alkali washing and RO water washing as in Example 1 so as to obtain the intended adsorbent, on which protein A was immobilized.

The electrical conductivity of the wash filtrate was measured using an electrical conductivity meter (ECTestr10 pure+ manufactured by Eutech Instruments). The quantity of IgG, which was the purification target substance, adsorbed on the obtained adsorbent was determined using the aforementioned method, and was found to be 46 mg relative to 1 mL of the adsorbent. The compressive stress of the obtained adsorbent was 0.017 MPa when compressed by 5%, 0.034 MPa when compressed by 10%, and not less than 0.054 MPa when compressed by 15%. In addition, the volume average particle diameter of the adsorbent was 101 μm.

Example 23

RO water was added to 57 mL of a porous cellulose base matrix (CK-A manufactured by Chisso Corporation) having a volume average particle diameter of 93 μm and a resin content of 6% to obtain a total volume of 85.5 mL, and the total volume of the mixture was transferred to a 250 mL plastic container. Next, sodium periodate (manufactured by Wako Pure Chemical Industries, Ltd.) was dissolved in RO water to obtain a solution containing 11.45 mg/mL of sodium periodate, and 57 mL of the aqueous sodium periodate solution was added to the plastic container. The mixture was allowed to react at 25° C. for 1 hour while being shaken at 100 rpm using a mixing rotor (variable mixing rotor VMR-5, manufactured by Iuchi Seieido Co., Ltd.) in an incubator (incubator LOW-TEMP ICB-151L, manufactured by Iwaki Glass Co., Ltd.). After the reaction, the porous base matrix was washed on a glass filter with a volume of RO water equivalent to 20 times the volume of the porous base matrix so as to obtain a formyl group-containing porous base matrix. The formyl group content of the obtained formyl group-containing porous base matrix was measured using the method mentioned above, and was found to be 5 μmol relative to 1 mL of the porous base matrix.

The formyl group-containing porous base matrix (51 mL) was substituted with 255 mL of a pH 10 buffer containing 0.5 M phosphoric acid and 0.15 M common salt (prepared from disodium hydrogen phosphate, sodium chloride, sodium hydroxide and RO water manufactured by Wako Pure Chemical Industries, Ltd.) on a glass filter (17G-2 manufactured by TOP). A pH 10 buffer containing 0.5 M phosphoric acid and 0.15 M common salt was added to the substituted formyl group-containing porous base matrix to obtain a total volume of 84.7 mL. The mixture was transferred to a 250 mL plastic container, and 7.76 mL of a protein A-containing solution (PNXL28 manufactured by Kaneka Corporation) containing 52.6 mg/mL of protein A obtained using the method disclosed in PCT Publication No. WO 2006/004067 was added thereto. The mixture was allowed to react at 4° C. for 12 hours while being shaken at 100 rpm using a mixing rotor (variable mixing rotor VMR-5, manufactured by Iuchi Seieido Co., Ltd.) in an incubator (incubator LOW-TEMP ICB-151L, manufactured by Iwaki Glass Co., Ltd.). The pH of the reaction liquid after the reaction was adjusted to 8 using 4 M hydrochloric acid (prepared from hydrochloric acid and RO water manufactured by Wako Pure Chemical Industries, Ltd.), and 0.145 g of sodium borohydride (manufactured by Wako Pure Chemical Industries, Ltd.) was added thereto. The mixture was allowed to react under gentle stirring at 4° C. After 1 hour, a further 0.145 g of sodium borohydride was added, and the mixture was gently stirred at 4° C. The operation was repeated so that sodium borohydride was added a total of five times. After the reaction, the absorbance of the reaction liquid at the absorption maximum near 276 nm was measured; as a result, it was found that the introduced quantity of protein A affinity ligand was 5.4 mg relative to 1 mL of the porous base matrix.

After the reaction, the porous base matrix was subjected to the same acid washing, alkali washing and RO water washing as in Example 1 so as to obtain the intended adsorbent, on which protein A was immobilized.

The electrical conductivity of the wash filtrate was measured using an electrical conductivity meter (ECTestr10 pure+ manufactured by Eutech Instruments). The quantity of IgG, which was the purification target substance, adsorbed on the obtained adsorbent was determined using the aforementioned method, and was found to be 35 mg relative to 1 mL of the adsorbent.

Comparative Example 2

RO water was added to 175 mL of a porous cellulose base matrix having a volume average particle diameter of 93 μm and a resin content of 6% (CK-A, manufactured by Chisso Corporation) to obtain a total volume of 221 mL. The mixture was placed in a plastic container (500 mL, manufactured by Sanplatec Co., Ltd.), and 64 mL of a 2 M aqueous solution of sodium hydroxide (prepared from sodium hydroxide and RO water manufactured by Wako Pure Chemical Industries, Ltd.) was added thereto. The mixture was heated at 40° C. for 30 minutes. After the temperature of the liquid reached 40° C., 11 mL of epichlorohydrin (manufactured by Wako Pure Chemical Industries, Ltd.) was added thereto, and the mixture was allowed to react at 40° C. for 2 hours while being shaken at 100 rpm using a constant temperature stirrer (thermostatic water bath T-25, manufactured by Thomas Kagaku Co., Ltd). After completion of the reaction, the porous base matrix was washed on a glass filter (26G-2 manufactured by TOP) with a volume of RO water equivalent to 20 times the volume of the porous base matrix so as to obtain an epoxidized porous base matrix.

The obtained epoxidized porous base matrix (6.6 mL) was subjected to suction filtration, i.e. suction drying, on a glass filter (3G-2 manufactured by TOP) for 15 minutes, and 1.5 g of the suction dried porous base matrix was weighed into a screw tube (manufactured by Maruemu Corporation), and 4.5 mL of a 1.3 M aqueous solution of sodium thiosulfate (prepared from sodium thiosulfate and RO water manufactured by Wako Pure Chemical Industries, Ltd.) was added thereto. After being heated at 45° C. for 30 minutes, the mixture was transferred to a 100 mL glass beaker together with 45 mL of RO water, and several drops of a 1% solution of phenolphthalein (prepared from phenolphthalein and ethanol manufactured by Wako Pure Chemical Industries, Ltd.) were added thereto. The epoxy group content was determined by titrating with 0.01 N hydrochloric acid (for volumetric analysis, manufactured by Wako Pure Chemical Industries, Ltd.), and was found to be 7 μmol relative to 1 g of the suction dried porous base matrix. In addition, the epoxy group content was 5.7 μmol relative to 1 mL of gel.

Next, RO water was added to the obtained epoxidized porous base matrix so as to obtain a volume that was twice that of the crosslinked porous base matrix. The mixture was placed in a glass beaker (1 L), sealed with two sheets of aluminum foil, and then heated at 120° C. for 40 minutes using an autoclave (manufactured by Sakura). After the mixture was allowed to cool to room temperature, the porous base matrix was washed on a glass filter (17G-2 manufactured by TOP) with a volume of RO water equivalent to 5 times the volume of the porous base matrix so as to obtain a porous base matrix in which the epoxy group was converted into glyceryl group.

RO water was added to 83 mL of the washed porous base matrix to obtain a total volume of 125 mL. The mixture was then placed in a plastic container (500 mL, manufactured by Sanplatec Co., Ltd.). Next, 119 mg of sodium periodate (manufactured by Wako Pure Chemical Industries, Ltd.) was dissolved in 83 mL of RO water, and the aqueous sodium periodate solution was added to the plastic container, and the mixture was allowed to react at 25° C. for 1 hour while being shaken at 100 rpm using a mixing rotor (variable mixing rotor VMR-5, manufactured by Iuchi Seieido Co., Ltd.) in an incubator (incubator LOW-TEMP ICB-151L, manufactured by Iwaki Glass Co., Ltd.). After the reaction, the porous base matrix was washed on a glass filter (26G-2 manufactured by TOP) with a volume of RO water equivalent to 20 times the volume of the porous base matrix so as to obtain a formyl group-containing porous base matrix. The formyl group content of the obtained formyl group-containing porous base matrix was measured using the method mentioned above, and was found to be 7 μmol relative to 1 mL of the porous base matrix.

The formyl group-containing porous base matrix (21 mL) was substituted with 63 mL of a pH 10 buffer containing 0.5 M phosphoric acid and 0.15 M common salt (prepared from disodium hydrogen phosphate, sodium chloride, sodium hydroxide and RO water manufactured by Wako Pure Chemical Industries, Ltd.) on a glass filter (17G-2 manufactured by TOP). A pH 10 buffer containing 0.5 M phosphoric acid and 0.15 M common salt was added to the substituted formyl group-containing porous base matrix to obtain a total volume of 35 mL. The mixture was placed in a plastic container (100 mL, manufactured by Sanplatec Co., Ltd.), and 3.16 mL of a protein A-containing solution (PNXL28 manufactured by Kaneka Corporation) containing 52.6 mg/mL of protein A obtained using the method disclosed in PCT Publication No. WO 2006/004067 was added thereto. The mixture was allowed to react at 4° C. for 12 hours while being shaken at 100 rpm using a mixing rotor (variable mixing rotor VMR-5, manufactured by Iuchi Seieido Co., Ltd.) in an incubator (incubator LOW-TEMP ICB-151L, manufactured by Iwaki Glass Co., Ltd.). The pH of the reaction liquid after the reaction was adjusted to 8 using 4 M hydrochloric acid (prepared from hydrochloric acid and RO water manufactured by Wako Pure Chemical Industries, Ltd.), and 59 mg of sodium borohydride was added thereto, and the mixture was allowed to react under gentle shaking at 4° C. for 1 hour. After the reaction, the absorbance of the reaction liquid at the absorption maximum near 277 nm was measured; as a result, it was found that the introduced quantity of protein A affinity ligand was 5.3 mg relative to 1 mL of the porous base matrix.

After the reaction, the porous base matrix was washed on a glass filter (25G-2 manufactured by TOP) with a volume of RO water equivalent to 20 times the volume of the porous base matrix. RO water was then added to the porous base matrix so as to obtain a volume which was twice that of the porous base matrix, and the mixture was placed in a plastic container (100 mL, manufactured by Sanplatec Co., Ltd.). Next, 3.26 g of sodium borohydride was dissolved in RO water to obtain a volume of 21 mL, and the total quantity of the solution was added to the plastic container gradually over a period of 5 hours. After the reaction, the porous base matrix was subjected to the same acid washing, alkali washing and RO water washing as in Example 1 so as to obtain the intended adsorbent, on which protein A was immobilized.

The quantity of IgG, which was the purification target substance, adsorbed on the obtained adsorbent for purification was determined using the aforementioned method, and was found to be 46 mg relative to 1 mL of the adsorbent.

Measurement of Quantity of Ligand Leakage

Solution Preparation

A pH 7.4 phosphate buffer (manufactured by Sigma) as liquid A, a 35 mM solution of sodium acetate having pH of 3.5 (prepared from acetic acid, sodium acetate and RO water manufactured by Wako Pure Chemical Industries, Ltd.) as liquid B, a 1 M acetic acid solution (prepared from acetic acid and RO water manufactured by Wako Pure Chemical Industries, Ltd.) as liquid C, a 1 mg/mL solution of IgG (prepared from Gammagard manufactured by Baxter and liquid A) as liquid D, 6 M urea as liquid E, a liquid obtained by adding a surfactant (polyoxyethylene (20) sorbitan monolaurate manufactured by Wako Pure Chemical Industries, Ltd.) to liquid A at a concentration of 0.2 vol % relative to liquid A as liquid F, and a 2 M solution of tris(hydroxymethyl)aminomethane (prepared from tris(hydroxymethyl)aminomethane manufactured by Sigma and RO water) as a neutralizing solution were prepared, and degassed before use.

Charging and Preparation

Biologic LP system (manufactured by BIO-RAD) was used as a column chromatography apparatus, and a 22 μm mesh was fitted to a column having a diameter of 0.5 cm and a height of 15 cm. Each of the protein A-immobilized adsorbents (3 mL) obtained in the Examples and Comparative examples was placed therein, and was charged by flushing with a 20% aqueous ethanol solution (prepared from ethanol and RO water manufactured by Wako Pure Chemical Industries, Ltd.) for 1 hour at a linear speed of 400 cm/h. A 5 ml sampling tube was set in a fraction collector, and the neutralizing solution was placed in advance in a tube for sampling the eluate.

Washing

The adsorbents of Examples 2-20 were flushed with liquid F, liquid B, liquid A, liquid C and liquid E in that order at a linear speed of 300 cm/h with a volume equivalent to 3 times the volume of the adsorbent for each liquid. The flushing cycle was repeated six times.

IgG Preparation

Liquid A (9 mL) was flushed and liquid D was then flushed under UV monitoring until the IgG breakthrough was 10%. Next, 30 mL of liquid A was flushed and 30 mL of liquid B was flushed in order to elute the IgG. Next, 9 mL of liquid C and 9 mL of liquid E were flushed. The operation after completion of the adsorbent charging was repeated a further two times, and the quantity of IgG and the quantity of the ligand in the eluates were measured.

As a result, the quantity of ligand relative to the quantity of IgG in the purified IgG was 51 ppm the first time, 24 ppm the second time and 20 ppm the third time, and the average value was 32 ppm, when the adsorbent of Example 1 was used; and when the adsorbents of Examples 2-20 were used, the average values calculated from the first to the third times were not higher than 100 ppm. The quantity of ligand relative to the quantity of IgG in the purified IgG was 122 ppm the first time, 87 ppm the second time and 119 ppm the third time, and the average value was 109 ppm, when the adsorbent of Comparative example 1 was used.

In addition, the quantity of ligand relative to the quantity of IgG in the purified IgG was 76 ppm the first time, 57 ppm the second time and 56 ppm the third time, and the average value was 63 ppm, when the adsorbent of Example 21 was used; the quantity of ligand relative to the quantity of IgG in the purified IgG was 56 ppm the first time when the adsorbent of Example 22; and the quantity of ligand relative to the quantity of IgG in the purified IgG was 49 ppm the first time when adsorbent of Example 23. However, the quantity of ligand relative to the quantity of IgG in the purified IgG was 122 ppm the first time, 87 ppm the second time and 119 ppm the third time, and the average value was 109 ppm, when the adsorbent of comparative example 2 was used.

In addition, the degree of dynamic IgG adsorption relative to 1 mL of the adsorbent (5% dynamic binding capacity) obtained according to the measurements was 36 mg the first time, 35 mg the second time and 35 mg the third time in Example 1; 36 mg the first time, 36 mg the second time and 36 mg the third time in Comparative example 1; and was such that Example 21>Example 22≈Comparative example 2≥Example 23.

The invention claimed is:

1. A method for producing a porous base matrix having a formyl group, comprising steps of allowing a halohydrin or a bis- or higher-functional epoxy compound to act on a raw material porous base matrix in order to introduce an epoxy group to the raw material porous base matrix, transforming the epoxy group into a glyceryl group, allowing a periodate salt to act on the glyceryl group in order to transform the glyceryl group into a monoformyl group, allowing a five-membered ring sugar containing at least an amino group or a six-membered ring sugar containing at least an amino group to react with the epoxy group and the monoformyl group in order to introduce a group represented by the general formula (1):

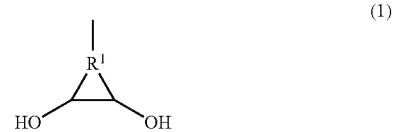

wherein, $R^1$ represents a group forming the sugar with —CH(OH)—CH(OH)—, transforming the group (1) with a periodate salt into a group represented by the general formula (2):

wherein, $R^1$ is the same as the above.

2. The method for production according to claim 1, wherein the porous base matrix precursor has 5 μmol or more of the group represented by the general formula (1) per 1 mL of the porous base matrix precursor.

3. The method for production according to claim 1, wherein the group represented by the general formula (2) is derived by reacting a periodate with the group represented by the general formula (1).

4. An adsorbent, wherein an affinity ligand is bound on a porous base matrix having a formyl group, wherein the porous base matrix is produced by steps of:

allowing a halohydrin or a bis- or higher-functional epoxy compound to act on a raw material porous base matrix in order to introduce an epoxy group to the raw material porous base matrix, transforming the epoxy group into a glyceryl group, allowing a periodate salt to act on the glyceryl group in order to transform the glyceryl group into a monoformyl group, allowing a five-membered ring sugar containing at least an amino group or a six-membered ring sugar containing at least an amino group to react with the epoxy group and the monoformyl group in order to introduce a group represented by the general formula (1):

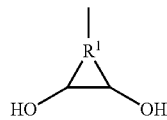

(1)

wherein, $R^1$ represents a group forming the sugar containing at least the amino group with —CH(OH)—CH(OH)—, transforming the group (1) with a periodate salt into a group represented by the general formula (2):

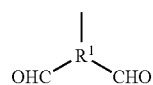

(2)

wherein $R^1$ is the same as above, and wherein the porous base matrix has the above group represented by the general formula (2) for a spacer.

5. The adsorbent according to claim 4, wherein the amount of the affinity ligand is 1 mg or more and 1000 mg or less per 1 mL of the porous base matrix.

6. The adsorbent according to claim 4, having a group represented by the general formula (3) or (4):

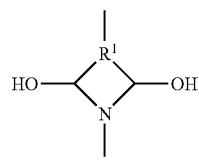

(3)

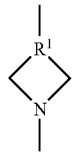

(4)

wherein, $R^1$ represents a group forming a six-membered ring sugar containing at least an amino group or a seven-membered ring sugar containing at least an amino group with the nitrogen atom.

7. The adsorbent according to claim 4, wherein the affinity ligand is protein A.

8. The adsorbent according to claim 4, wherein the concentration of the ligand leaked into an object from the adsorbent is 100 ppm or less.

9. The adsorbent according to claim 4, wherein the absorbed amount of the object to be purified is 1 mg or more per 1 mL of the adsorbent.

10. A method for producing an adsorbent, comprising a step of binding an affinity ligand on a porous base matrix having a formyl group, wherein the porous base matrix is produced by steps of:

allowing a halohydrin or a bis- or higher-functional epoxy compound to act on a raw material porous base matrix in order to introduce an epoxy group to the raw material porous base matrix, transforming the epoxy group into a glyceryl group, allowing a periodate salt to act on the glyceryl group in order to transform the glyceryl group into a monoformyl group, allowing a five-membered ring sugar containing at least an amino group or a six-membered ring sugar containing at least an amino group to react with the epoxy group and the monoformyl group in order to introduce a group represented by the general formula (1):

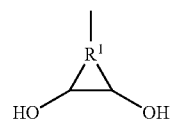

(1)

wherein, $R^1$ represents a group forming the sugar containing at least the amino group with —CH(OH)—CH(OH)—, transforming the group (1) with a periodate salt into a group represented by the general formula (2):

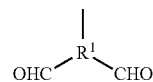

(2)

wherein $R^1$ is the same as above, and wherein the porous base matrix has the above group represented by the general formula (2) for a spacer.

11. A method for purifying an immunoglobulin, comprising a step of using the adsorbent according to claim 7.

* * * * *